United States Patent
Smith et al.

(10) Patent No.: US 9,220,478 B2
(45) Date of Patent: Dec. 29, 2015

(54) CONCAVE ULTRASOUND TRANSDUCERS AND 3D ARRAYS

(71) Applicant: Maui Imaging, Inc., Sunnyvale, CA (US)

(72) Inventors: David M. Smith, Lodi, CA (US); Donald F. Specht, Los Altos, CA (US); Linda V. Cabrera, Cypress, CA (US); Kenneth D. Brewer, Santa Clara, CA (US); David J. Specht, San Jose, CA (US)

(73) Assignee: MAUI IMAGING, INC., Sunnyvale, CA (US)

( * ) Notice: Subject to any disclaimer, the term of this patent is extended or adjusted under 35 U.S.C. 154(b) by 0 days.

(21) Appl. No.: 14/595,083

(22) Filed: Jan. 12, 2015

(65) Prior Publication Data

US 2015/0157294 A1  Jun. 11, 2015

Related U.S. Application Data

(63) Continuation of application No. 13/272,105, filed on Oct. 12, 2011.

(60) Provisional application No. 61/392,896, filed on Oct. 13, 2010.

(51) Int. Cl.
*A61B 8/00* (2006.01)
*G01S 15/89* (2006.01)
(Continued)

(52) U.S. Cl.
CPC .............. *A61B 8/4494* (2013.01); *A61B 8/145* (2013.01); *A61B 8/4444* (2013.01); *A61B 8/4483* (2013.01); *A61B 8/461* (2013.01); *A61B 8/467* (2013.01); *A61B 8/523* (2013.01);
(Continued)

(58) Field of Classification Search
CPC ........................ A61B 8/4483; A61B 8/4494
See application file for complete search history.

(56) References Cited

U.S. PATENT DOCUMENTS

| 3,174,286 A | 3/1965 | Erickson |
|---|---|---|
| 3,895,381 A | 7/1975 | Kock |

(Continued)

FOREIGN PATENT DOCUMENTS

| CN | 101190134 A | 6/2008 |
|---|---|---|
| CN | 102123668 | 7/2011 |

(Continued)

OTHER PUBLICATIONS

Li et al.; An efficient speckle tracking algorithm for ultrasonic imaging; 24; pp. 215-228; Oct. 1, 2002.

(Continued)

*Primary Examiner* — Rochelle Turchen
(74) *Attorney, Agent, or Firm* — Shay Glenn LLP

(57) ABSTRACT

A Multiple Aperture Ultrasound Imaging (MAUI) probe or transducer is uniquely capable of simultaneous imaging of a region of interest from separate apertures of ultrasound arrays. Some embodiments provide systems and methods for designing, building and using ultrasound probes having continuous arrays of ultrasound transducers which may have a substantially continuous concave curved shape in two or three dimensions (i.e., concave relative to an object to be imaged). Other embodiments herein provide systems and methods for designing, building and using ultrasound imaging probes having other unique configurations, such as adjustable probes and probes with variable configurations.

10 Claims, 20 Drawing Sheets

(51) Int. Cl.
   *A61B 8/08*   (2006.01)
   *A61B 8/14*   (2006.01)
   *B06B 1/06*   (2006.01)
   *G01S 7/52*   (2006.01)

(52) U.S. Cl.
   CPC ............ *A61B 8/5207* (2013.01); *G01S 7/5205* (2013.01); *G01S 15/892* (2013.01); *G01S 15/8913* (2013.01); *G01S 15/8927* (2013.01); *G01S 15/8929* (2013.01); *G01S 15/8934* (2013.01); *A61B 8/14* (2013.01); *B06B 1/0622* (2013.01); *G01S 7/52084* (2013.01)

(56) References Cited

U.S. PATENT DOCUMENTS

| | | |
|---|---|---|
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,259,733 A | 3/1981 | Taner et al. |
| 4,271,842 A | 6/1981 | Specht et al. |
| 4,325,257 A | 4/1982 | Kino et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,539,847 A | 9/1985 | Paap |
| 4,566,459 A | 1/1986 | Umemura et al. |
| 4,567,768 A | 2/1986 | Satoh et al. |
| 4,662,222 A | 5/1987 | Johnson |
| 4,669,482 A | 6/1987 | Ophir |
| 4,682,497 A | 7/1987 | Sasaki |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 5,050,588 A | 9/1991 | Grey et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,355,888 A | 10/1994 | Kendall |
| 5,398,216 A | 3/1995 | Hall et al. |
| 5,409,010 A | 4/1995 | Beach et al. |
| 5,442,462 A | 8/1995 | Guissin |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A * | 2/1998 | Lu et al. ............ 600/447 |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A * | 8/1998 | Barabash et al. ............. 600/443 |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 * | 3/2001 | Shokrollahi et al. .......... 600/438 |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |

(56) References Cited

U.S. PATENT DOCUMENTS

| | | |
|---|---|---|
| 6,551,246 B1 | 4/2003 | Ustuner et al. |
| 6,565,510 B1 | 5/2003 | Haider |
| 6,585,647 B1 | 7/2003 | Winder |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | KrÖNing et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,277,383 B2 | 10/2012 | Specht |
| 8,279,705 B2 | 10/2012 | Choi et al. |
| 8,412,307 B2 | 4/2013 | Willis et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,532,951 B2 | 9/2013 | Roy et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0161299 A1 | 10/2002 | Prater et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1* | 9/2005 | Freiburger .................... 600/453 |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |

(56) References Cited

U.S. PATENT DOCUMENTS

| | | |
|---|---|---|
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262291 A1 | 11/2006 | Hess et al. |
| 2006/0262961 A1 | 11/2006 | Holsing et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0103393 A1* | 5/2008 | Specht .................. 600/437 |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0217124 A1 | 8/2010 | Cooley |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0201933 A1 | 8/2011 | Specht et al. |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0035482 A1 | 2/2012 | Kim et al. |
| 2012/0036934 A1 | 2/2012 | Kröning et al. |
| 2012/0057428 A1 | 3/2012 | Specht et al. |
| 2012/0085173 A1 | 4/2012 | Papadopoulos et al. |
| 2012/0095343 A1 | 4/2012 | Smith et al. |
| 2012/0095347 A1 | 4/2012 | Adam et al. |
| 2012/0101378 A1 | 4/2012 | Lee |
| 2012/0114210 A1 | 5/2012 | Kim et al. |
| 2012/0116226 A1 | 5/2012 | Specht |
| 2012/0121150 A1 | 5/2012 | Murashita |
| 2012/0137778 A1 | 6/2012 | Kitazawa et al. |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0172743 A1 | 7/2013 | Brewer et al. |

(56) References Cited

U.S. PATENT DOCUMENTS

| | | |
|---|---|---|
| 2013/0218012 A1 | 8/2013 | Specht et al. |
| 2013/0247350 A1 | 9/2013 | Specht et al. |
| 2013/0253325 A1 | 9/2013 | Call et al. |
| 2013/0258805 A1 | 10/2013 | Hansen et al. |
| 2013/0261463 A1 | 10/2013 | Chiang et al. |
| 2014/0043933 A1 | 2/2014 | Belevich et al. |
| 2014/0058266 A1 | 2/2014 | Call et al. |
| 2014/0073921 A1 | 3/2014 | Specht et al. |
| 2014/0135626 A1 | 5/2014 | Specht |
| 2014/0243673 A1 | 8/2014 | Anand et al. |
| 2014/0269209 A1 | 9/2014 | Smith et al. |
| 2015/0045668 A1 | 2/2015 | Smith et al. |

FOREIGN PATENT DOCUMENTS

| | | |
|---|---|---|
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 2356941 A1 | 8/2011 |
| EP | 1979739 | 10/2011 |
| EP | 2385391 A2 | 11/2011 |
| EP | 2294400 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | S49-11189 A | 1/1974 |
| JP | S54-44375 A | 4/1979 |
| JP | S55-103839 A | 8/1980 |
| JP | 59-101143 A | 6/1984 |
| JP | S59-174151 A | 10/1984 |
| JP | S60-13109 U | 1/1985 |
| JP | S60-68836 A | 4/1985 |
| JP | 2-501431 | 5/1990 |
| JP | 4-67856 | 3/1992 |
| JP | 05-042138 A | 2/1993 |
| JP | 6-125908 A | 5/1994 |
| JP | 7-051266 A | 2/1995 |
| JP | 08-252253 | 10/1996 |
| JP | 9-103429 A | 4/1997 |
| JP | 9-201361 A | 8/1997 |
| JP | 10-216128 A | 8/1998 |
| JP | 11-089833 A | 4/1999 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2005-523792 | 8/2005 |
| JP | 2005-526539 | 9/2005 |
| JP | 2006-122657 A | 5/2006 |
| JP | 2008-122209 | 5/2008 |
| JP | 2008-513763 A | 5/2008 |
| JP | 2008-259541 A | 10/2008 |
| JP | 20105375 | 1/2010 |
| KR | 1020090103408 | 10/2009 |
| WO | WO92/18054 A1 | 10/1992 |
| WO | WO98/00719 A2 | 1/1998 |
| WO | WO02/084594 A2 | 10/2002 |
| WO | WO2005/009245 A1 | 2/2005 |
| WO | WO2006/114735 A1 | 11/2006 |
| WO | WO2007/127147 A2 | 11/2007 |
| WO | WO2009/060182 A2 | 5/2009 |
| WO | WO2010/095094 A1 | 8/2010 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO 2012/049124 A2 | 4/2012 |
| WO | WO 2012/049612 A2 | 4/2012 |
| WO | WO 2012/078639 A1 | 6/2012 |
| WO | WO 2012/091280 A1 | 7/2012 |
| WO | WO 2012/112540 A2 | 8/2012 |
| WO | WO 2012/131340 A2 | 10/2012 |
| WO | WO2012/160541 A2 | 11/2012 |

OTHER PUBLICATIONS

UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.

Wikipedia; Curve fitting; 5 pages; retrieved from the internet (http:en.wikipedia.org/wiki/Curve_fitting) Dec. 19, 2010.

Specht et al.; U.S. Appl. No. 14/279,052 entitled "Ultrasound imaging using apparent point-source transmit transducer," filed May 15, 2014.

Ledesma-Carbayo et al.; Spatio-temporal nonrigid registration for ultrasound cardiac motion estimation; IEEE Trans. On Medical Imaging; vol. 24; No. 9; Sep. 2005.

Leotta et al.; Quantitative three-dimensional echocardiography by rapid imaging . . . ; J American Society of Echocardiography; vol. 10; No. 8; pp. 830-839; Oct. 1997.

Montaldo et al.; Building three-diminsional images using a time-reversal chaotic cavity; IEEE Trans. On Ultrasonics, Ferroelectrics, and Frequency Control; 52(9); pp. 1489-1497; Sep. 2005.

Morrison et al.; A probabilistic neural network based image segmentation network for magnetic resonance images; Proc. Conf. Neural Networks; Baltimore, MD; vol. 3; pp. 60-65; Jun. 1992.

Nadkarni et al.; Cardiac motion synchronization for 3D cardiac ultrasound imaging; Ph.D. Dissertation, University of Western Ontario; Jun. 2002.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Sakas et al.; Preprocessing and volume rendering of 3D ultrasonic data; IEEE Computer Graphics and Applications; pp. 47-54, Jul. 1995.

Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. On Neural Networks; vol. 2.; No. 6; Nov. 1991.

Specht, D.F.; Blind deconvolution of motion blur using LMS inverse filtering; Lockheed Independent Research (unpublished); Jun. 23, 1975.

(56) References Cited

OTHER PUBLICATIONS

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

Wikipedia; Speed of sound; 17 pages; retrieved from the internet (http:en.wikipedia.org/wiki/Speed_of_sound) Feb. 15, 2011.

Abeysekera et al.; Alignment and calibration of dual ultrasound transducers using a wedge phantom; Ultrasound in Medicine and Biology; 37(2); pp. 271-279; Feb. 2011.

Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb 28, 2008.

Chen et al.; Maximum-likelihood source localization and unknown sensor location estimation for wideband signals in the near-field; IEEE Transactions on Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.

Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.

Hsu et al.; Real-time freehand 3D ultrasound calibration; CUED/F-INFENG/TR 565; Department of Engineering, University of Cambridge, United Kingdom; 14 pages; Sep. 2006.

Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.

Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.

Urban et al; Implementation of vibro-acoustography on a clinical ultrasound system; IEEE Transactions on Ultrasonics, Ferroelectrics, and Frequency Control; 58(6); pp. 1169-1181; Jun. 2011 (Author Manuscript).

Urban et al; Implementation of vibro-acoustography on a clinical ultrasound system; IEEE Ultrasonics Symposium (IUS); pp. 326-329; Oct. 14, 2010.

Wang et al.; Photoacoustic tomography of biological tissues with high cross-section resolution: reconstruction and experiment; Medical Physics; 29(12); pp. 2799-2805; Dec. 2002.

Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.

\* cited by examiner

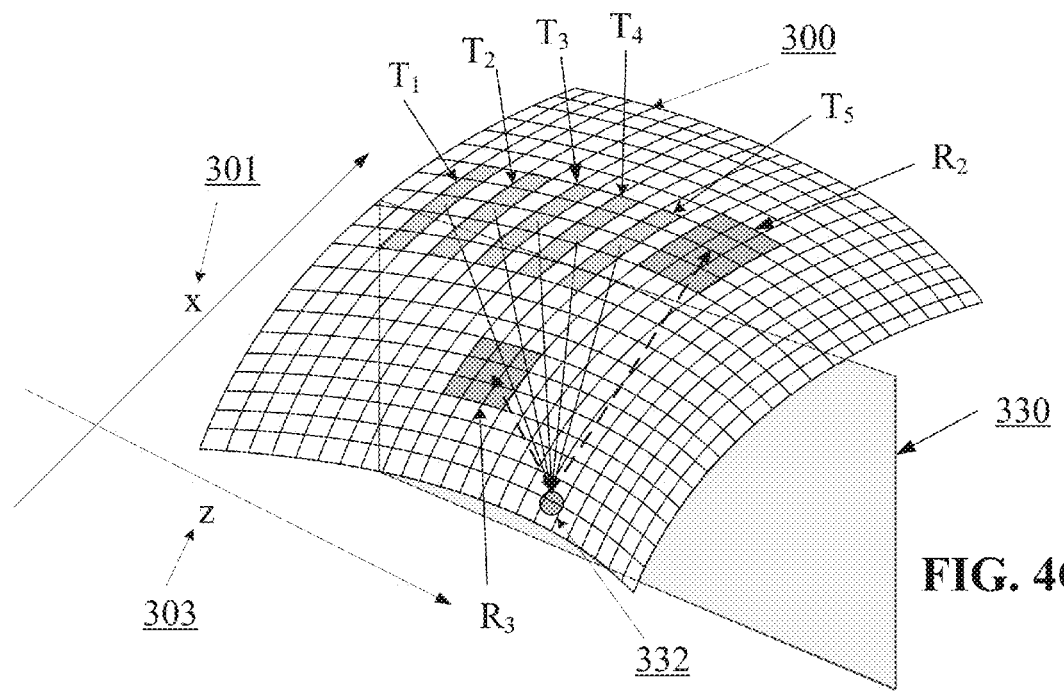
FIG. 4C
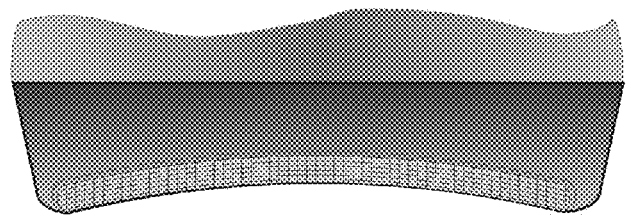
FIG. 4D
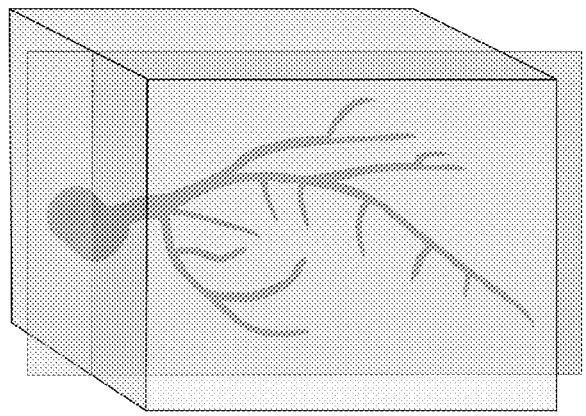

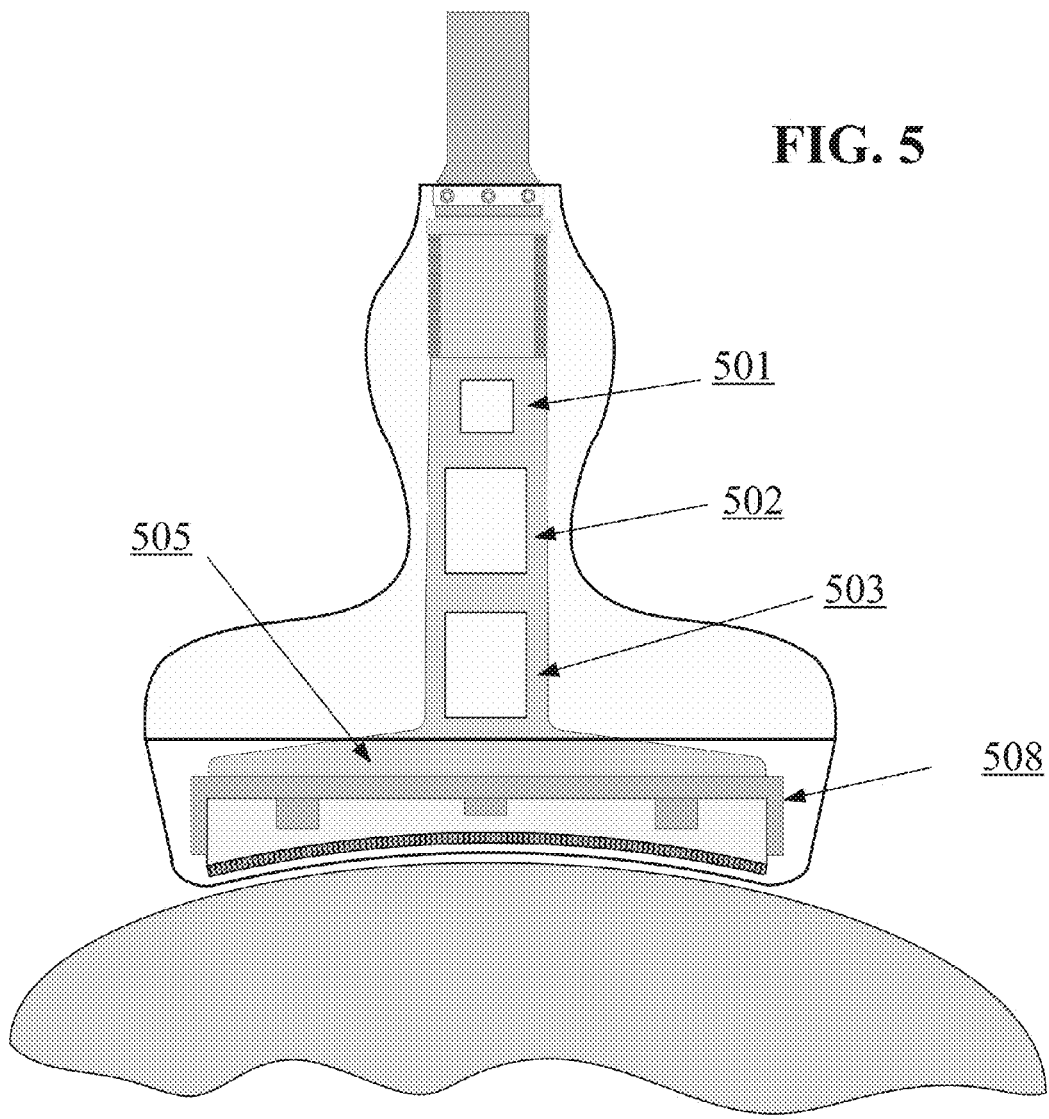

CONCAVE ULTRASOUND TRANSDUCERS AND 3D ARRAYS

CROSS REFERENCE TO RELATED APPLICATIONS

This application is a continuation of U.S. patent application Ser. No. 13/272,105, filed Oct. 12, 2011, which application claims the benefit under 35 U.S.C. 119 of U.S. Provisional Patent Application No. 61/392,896, filed Oct. 13, 2010, titled "Multiple Aperture Medical Ultrasound Transducers," which applications are incorporated herein by reference.

This application is related to U.S. Pat. No. 8,007,439, titled "Method and Apparatus to Produce Ultrasonic Images Using Multiple Apertures", and PCT Application No. PCT/US2009/053096, filed Aug. 7, 2009, titled "Imaging with Multiple Aperture Medical Ultrasound and Synchronization of Add-on Systems." This application is also related to U.S. patent application Ser. No. 12/760,327 filed Apr. 14, 2010, titled "Multiple Aperture Ultrasound Array Alignment Fixture", and U.S. patent application Ser. No. 12/760,375, filed Apr. 14, 2010, titled "Universal Multiple Aperture Medical Ultrasound Probe", and U.S. patent application Ser. No. 13/029,907, filed Feb. 17, 2011, titled "Point Source Transmission and Speed-of-Sound Correction Using Multi-Aperture Ultrasound Imaging".

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to imaging techniques used in medicine, and more particularly to medical ultrasound, and still more particularly to an apparatus for producing ultrasonic images using multiple apertures.

BACKGROUND

In conventional ultrasonic imaging, a focused beam of ultrasound energy is transmitted into body tissues to be examined and the returned echoes are detected and plotted to form an image. In echocardiography, the beam is usually stepped in increments of angle from a center probe position, and the echoes are plotted along lines representing the paths of the transmitted beams. In abdominal ultrasonography, the beam is usually stepped laterally, generating parallel beam paths, and the returned echoes are plotted along parallel lines representing these paths.

The basic principles of conventional ultrasonic imaging are described in the first chapter of *Echocardiography*, by Harvey Feigenbaum (Lippincott Williams & Wilkins, 5th ed., Philadelphia, 1993). It is well known that the average velocity v of ultrasound in human tissue is about 1540 m/sec, the range in soft tissue being 1440 to 1670 m/sec (P. N. T. Wells, *Biomedical Ultrasonics*, Academic Press, London, New York, San Francisco, 1977). Therefore, the depth of an impedance discontinuity generating an echo can be estimated by the round-trip time for the echo multiplied by v/2, and the amplitude is plotted at that depth along a line representing the path of the beam. After this has been done for all echoes along all beam paths, an image is formed. The gaps between the scan lines are typically filled in by interpolation.

In order to insonify the body tissues, a beam formed by an array of transducer elements is scanned over the tissues to be examined. Traditionally, the same transducer array is used to detect the returning echoes. The use of the same transducer array to both produce the beam and detect returning echoes is one of the most significant limitations in the use of ultrasonic imaging for medical purposes; this limitation produces poor lateral resolution. Theoretically, the lateral resolution could be improved by increasing the aperture of the ultrasonic probe, but the practical problems involved with aperture size increase have kept apertures small and lateral resolution diminished. Unquestionably, ultrasonic imaging has been very useful even with this limitation, but it could be more effective with better resolution.

In the practice of cardiology, for example, the limitation on single aperture size is dictated by the space between the ribs (the intercostal spaces). For scanners intended for abdominal and other use, the limitation on aperture size is a serious limitation as well. The problem is that it is difficult to keep the elements of a large aperture array in phase because the speed of ultrasound transmission varies with the type of tissue between the probe and the area of interest. According to Wells (*Biomedical Ultrasonics*, as cited above), the transmission speed varies up to plus or minus 10% within the soft tissues. When the aperture is kept small, the intervening tissue is assumed to be homogeneous, and any variation is consequently ignored. When the size of the aperture is increased to improve the lateral resolution, the additional elements of a phased array may be out of phase and may actually degrade the image rather than improve it.

In the case of abdominal imaging, it has also been recognized that increasing the aperture size could improve the lateral resolution. Although avoiding the ribs is not a problem, beam forming using a sparsely filled array and, particularly, tissue speed variation needs to be compensated. With single aperture ultrasound probes, it has been commonly assumed that the beam paths used by the elements of the transducer array are close enough together to be considered similar in tissue density profile, and therefore that no compensation was necessary. The use of this assumption, however, severely limits the size of the aperture that can be used.

The problems of limited total aperture size have been addressed by the development of multiple aperture ultrasound imaging techniques as shown and described for example in U.S. Pat. No. 8,007,439, and US Patent Application Publication 2011/0201933.

SUMMARY OF THE DISCLOSURE

In one embodiment, an ultrasound imaging system is provided, comprising an ultrasound transducer array, the ultrasound transducer array having a concave curvature about at least one axis, a first transmit aperture in the ultrasound transducer array configured to insonify a scatterer with ultrasound energy, a first receive aperture in the ultrasound transducer array configured to receive ultrasound echoes from the scatterer, the first receive aperture being located apart from the first transmit aperture, and a control system in electronic communication with the ultrasound transducer array, the control system configured to access calibration data describing a position and orientation of the first transmit aperture and the first receive aperture, the control system configured to form an ultrasound image with the echoes received by the first receive aperture.

In some embodiments, the system further comprises a second receive aperture in the ultrasound transducer array configured to receive echoes from the scatterer, the second receive aperture being located apart from the first transmit aperture and the first receive aperture, wherein the control system is configured to access calibration data describing a position and orientation of the second receive aperture, and wherein the control system is configured to form an ultrasound image with the echoes received by the first and second receive apertures.

In some embodiments, the ultrasound transducer array has a concave curvature about at least two axes.

In one embodiment, the calibration data is stored in the control system. In other embodiments, the calibration data is stored remotely from the control system. In one embodiment, the calibration data is stored in a chip housed within a probe housing along with the array.

A method of ultrasound imaging is provided, comprising, transmitting ultrasound energy towards a scatterer with transmit aperture on an ultrasound transducer array having a concave curvature about at least one axis, receiving ultrasound echoes from the scatterer with a first receive aperture on the ultrasound transducer array, obtaining calibration data containing a position and orientation of ultrasound transducers in the first transmit aperture and the first receive aperture, and forming an ultrasound image with the ultrasound echoes received by the first receive aperture.

In some embodiments, the method further comprises receiving ultrasound echoes from the scatterer with a second receive aperture on the ultrasound transducer array; obtaining calibration data containing a position and orientation of ultrasound transducers in the second receive aperture, and forming an ultrasound image with the ultrasound echoes received by the first and second receive apertures.

Another ultrasound imaging system comprises an ultrasound transducer array; a first transmit aperture in the ultrasound transducer array configured to insonify a scatterer with ultrasound energy, a first receive aperture in the ultrasound transducer array configured to receive ultrasound echoes from the scatterer, the first receive aperture being located apart from the first transmit aperture, a second receive aperture in the ultrasound transducer array configured to receive ultrasound echoes from the scatterer, the second receive aperture being located apart from the first transmit aperture and the first receive aperture, and a control system in electronic communication with the ultrasound transducer array, the control system configured to change a total aperture size of the system by switching from receiving echoes with the first receive aperture to receiving echoes with the second receive aperture.

In one embodiment, the control system is configured to access calibration data describing a position and orientation of the first transmit aperture, the first receive aperture, and the second receive aperture, wherein the control system is configured to form an ultrasound image with the echoes received by the first and second receive apertures.

In some embodiments, the control system is configured to change the total aperture size automatically upon detection of an obstruction.

An ultrasound imaging system is also provided, comprising an ultrasound transducer array, a first transmit aperture in the ultrasound transducer array configured to insonify a scatterer with ultrasound energy; a second transmit aperture in the ultrasound transducer array configured to insonify the scatterer with ultrasound energy, a first receive aperture in the ultrasound transducer array configured to receive ultrasound echoes from the scatterer, the first receive aperture being located apart from the first transmit aperture; a second receive aperture in the ultrasound transducer array configured to receive ultrasound echoes from the scatterer, the second receive aperture being located apart from the first transmit aperture and the first receive aperture, and a control system in electronic communication with the ultrasound transducer array, the control system configured to change an aperture view angle of the system by switching from transmitting ultrasound energy with the first transmit aperture to transmitting ultrasound energy with the second transmit aperture, and switching from receiving echoes with the first receive aperture to receiving echoes with the second receive aperture, wherein a transmit/receive angle between the first transmit aperture and the first receive aperture is approximately the same as the transmit/receive angle between the second transmit aperture and the second receive aperture.

In one embodiment, the control system is configured to access calibration data describing a position and orientation of the first transmit aperture, the first receive aperture, and the second receive aperture, wherein the control system is configured to form an ultrasound image with the echoes received by the first and second receive apertures.

In another embodiment, the control system is configured to change the aperture view angle automatically upon detection of an obstruction.

A method of ultrasound imaging is provided, comprising transmitting ultrasound energy towards a scatterer with a first transmit aperture on an ultrasound transducer array having a concave curvature about at least one axis, receiving ultrasound echoes from the scatterer with a first receive aperture on the ultrasound transducer array, detecting an obstruction between the scatterer and the first receive aperture, and after detecting the obstruction, receiving ultrasound echoes from the scatterer with a second receive aperture on the ultrasound transducer array.

In some embodiments, the detecting step is performed by a sonographer. In other embodiments, the detecting step is performed automatically by a control system.

In one embodiment, the transducer array has a concave curvature about at least two axes.

In one embodiment, the after detecting step further comprises after detecting the obstruction, receiving ultrasound echoes from the scatterer with the second receive aperture on the ultrasound transducer array, wherein the obstruction is not located between the scatterer and the second receive aperture.

A method of ultrasound imaging is provided, comprising transmitting ultrasound energy towards a scatterer with a first transmit aperture on an ultrasound transducer array having a concave curvature about at least one axis, receiving ultrasound echoes from the scatterer with a first receive aperture on the ultrasound transducer array; detecting an obstruction between the scatterer and the first transmit aperture, and after detecting the obstruction, transmitting ultrasound energy towards the scatterer with a second transmit aperture on the ultrasound transducer array.

In one embodiment, the detecting step is performed by a sonographer. In another embodiment, the detecting step is performed automatically by a control system.

In some embodiments, the transducer array has a concave curvature about at least two axes.

Another embodiment of an ultrasound imaging device comprises a probe housing, at least two ultrasound transducer arrays disposed on our near the probe housing, and at least one hinge mechanism configured to couple each of the ultrasound transducer arrays to the probe housing, the hinge mechanisms configured to allow adjustment of the position or orientation of the ultrasound transducer arrays so as to conform to a physiology of interest.

In some embodiments, the device further comprises a locking mechanism configured to lock the hinge mechanisms.

A method of ultrasound imaging is provided, comprising placing an ultrasound imaging probe having at least two ultrasound arrays into contact with a patient, allowing each of the ultrasound arrays to individually conform to the physiology of the patient, locking the ultrasound arrays into a conformed configuration, calibrating the ultrasound imaging probe in the conformed configuration, and after the calibrating step, generating ultrasound images of the patient with the ultrasound imaging probe.

BRIEF DESCRIPTION OF THE FIGURES

FIG. 4C schematically illustrates an embodiment of a 3D array being used to collect data for a 2D transverse slice along the z axis. In this instance, a line of elements in the longitudinal axis x are being used to form transmit aperture $T_1$. Data along the transverse slice may be collected by elements located in receive aperture $R_2$. Multiple transmit apertures $T_1$ through $T_5$ are indicated that can be used along the length of the longitudinal slice to assist in data collection over time. Another receive aperture $R_3$ is indicated that can be used to collect either simultaneous data for the same transverse slice, or separate data for a different transverse slice.

FIG. 4D illustrates a data volume with a 2D longitudinal slice of data highlighted within the volume. This illustrates a capability of multiple aperture imaging to interchange volumetric 3D/4D imaging with higher resolution 2D imaging in near real time to allow for simultaneous presentation on a display.

FIG. 5 is a schematic view showing a concave curvilinear probe over a medium of tissue with a relatively large radius curvature (e.g., abdomen, pelvis, etc.).

DETAILED DESCRIPTION

Figure 1:
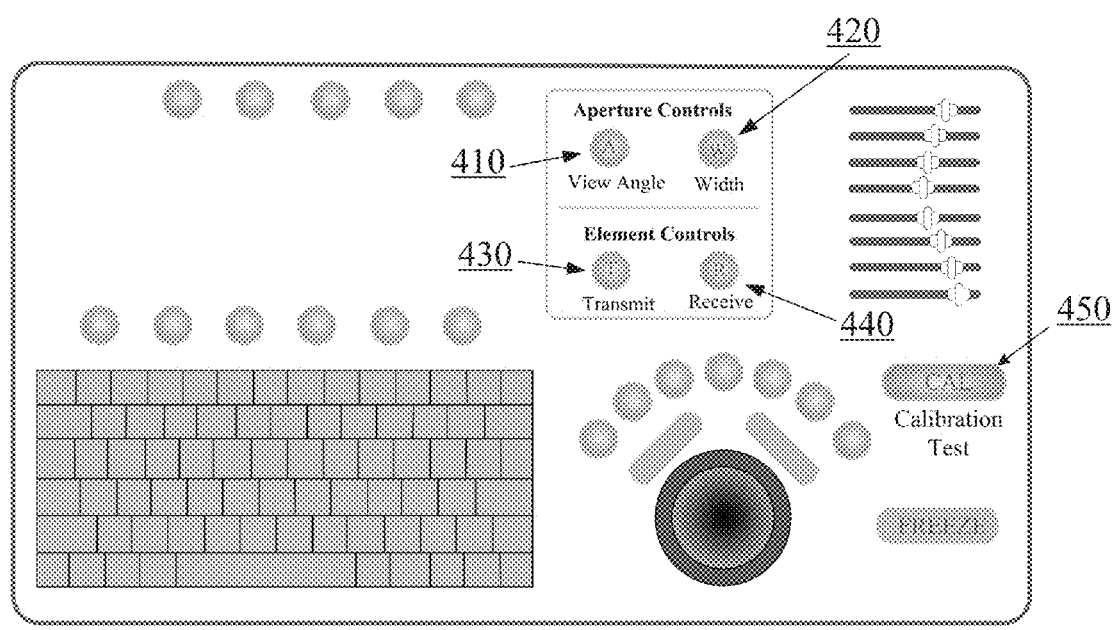
FIG. 1 is an illustration of an ultrasound system control panel with aperture view angle and aperture width controls.

Some embodiments herein provide systems and methods for designing, building and using ultrasound probes having continuous arrays of ultrasound transducers which may have a substantially continuous concave curved shape in two or three dimensions (i.e., concave relative to an object to be imaged). Other embodiments herein provide systems and methods for designing, building and using ultrasound imaging probes having other unique configurations, such as adjustable probes and probes with variable configurations.

The use of calibrated multiple aperture array or arrays combined with multiple aperture imaging methods allow for custom shaped, concave or even adjustable probes to be utilized in ultrasound imaging. Further, uniquely shaped ultrasound probe solutions are desirable in order to overcome the various shortcomings in the conventional rectangular linear, matrix or capacitive micromachined ultrasonic transducer or "CMUT" arrays in order to maintain information from an extended phased array "in phase", and to achieve a desired level of imaging lateral resolution.

In some embodiments, the ultrasound imaging system may be configured to allow for manual or automatic control of view angle, beam width and aperture size. This feature can be very advantageous when attempting to image tissue obscured by gas, bone or other ultrasound-opaque structures (e.g., vertebrae, joints, peripheral vasculature, organs located inside the thoracic cavity, etc.). With a shaped probe placed over the region of interest, the sonographer may control view angle of the target. Once the desired view angle is selected, the sonographer may electronically control aperture width in order to achieve the best resolution at the desired depth.

In one embodiment, there is a medical ultrasound apparatus having: (a) electronics configured for pulsing piezoelectric elements to transmit ultrasonic waves into human (or animal) tissue; (b) electronics configured to receive the resulting echo signals; (c) electronics configured to process the echo signals to form images; and (d) a probe having a plurality of receive elements within a receive subaperture, where the receive subaperture is sufficiently small that speed of sound variations in the paths from scatterers to each of the receive elements are sufficiently small to avoid phase cancelation when coherent averaging is used based on the assumption of uniform speed of sound profile over all paths. In addition, the probe may have a transmit element or plurality of transmit elements within a transmit subaperture, with at least one of the transmit elements being separated from the receive subaperture(s).

In another embodiment, the separation of transmit elements from elements of a receive subaperture is imposed for the purpose of increasing the total aperture width which determines the lateral resolution of the system without making the receive subaperture so large that phase cancellation degrades the image.

In another embodiment, the transmit subaperture may be sufficiently small that speed of sound variations in the paths from the transmit elements to scatterers are sufficiently small that the differences between the actual transmit times along these paths and the theoretical times assuming a constant nominal speed of sound vary from each other by a substantially small amount. In some embodiments, an acceptable variation in actual vs. theoretical travel times is less than one period of the ultrasound pulse. In some embodiments, the imaging control electronics insonifies the tissue to be imaged with a single ping, and beamforming and image processing electronics may form images by coherent addition of images formed by each single ping. In other embodiments, the beamforming and image processing electronics may form images by incoherent addition of images formed by each single ping.

Imaging transmit control electronics, beamforming electronics and image processing electronics may be collectively referred to herein as multiple aperture ultrasound imaging (or MAUI) electronics.

In still another embodiment, the MAUI electronics may form images by using image alignment such as cross correlation to align images and then adding the images incoherently.

In still another embodiment, the transmit aperture is not necessarily small and may include a receive subaperture. The MAUI electronics may insonify the tissue to be imaged with a single ping and may form images by incoherent addition of complete images formed by each single ping. Still further, the MAUI electronics may be configured to form images by using cross correlation to align images and then adding the images incoherently. In another embodiment, the system controller may include the processing capability where images formed with the different groups can be averaged together to form images with reduced noise and artifacts.

The improvements described herein are applicable to a wide variety of probe types including, for example, a general radiology concaved multiple aperture probe, a bracelet multiple aperture probe, a palm multiple aperture probe, and an adjustable multiple aperture probe.

In other alternative embodiments, aspects of the present provide for using unfocused pings for transmit, the transmit aperture can be much wider than the receive aperture and can enclose it.

In additional embodiments, receive elements of only one aperture can be used to construct an image when a transmit pulse or wave comes from an element or array of elements located outside and away from the receive elements' aperture, without using speed of sound correction in order to achieve a coherently averaged image.

Although several embodiments herein are described with reference to medical ultrasound imaging, the skilled artisan will recognize that features and advantages of the embodiments herein may also be achieved in non-medical ultrasound imaging applications, or in non-imaging applications of ultrasound.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micromachined ultrasound transducers (CMUT).

Transducers are often configured in arrays of multiple individual transducer elements. As used herein, the terms "transducer array" or "array" generally refers to a collection of transducer elements mounted to a common backing plate. Such arrays may have one dimension (1D), two dimensions (2D), 1.5 dimensions (1.5D) or three dimensions (3D). Other dimensioned arrays as understood by those skilled in the art may also be used. Transducer arrays may also be CMUT arrays. An element of a transducer array may be the smallest discretely functional component of an array. For example, in the case of an array of piezoelectric transducer elements, each element may be a single piezoelectric crystal or a single machined section of a piezoelectric crystal.

A 2D array can be understood to refer to a substantially planar structure comprising a grid of ultrasound transducer elements. Such a 2D array may include a plurality of individual elements (which may be square, rectangular or any other shape) arranged in rows and columns along the surface of the array. Often, a 2D array is formed by cutting element sections into a piezoelectric crystal.

As used herein, references to curved 1D, 1.5D or 2D transducer arrays are intended to describe ultrasound transducer arrays with curved surfaces having a curvature about only one axis (e.g., a transverse axis of a rectangular array). Thus, embodiments of 1D, 1.5D or 2D curved arrays may be described as partial cylindrical sections.

As used herein, the term "3D array" or "3D curved array" may be understood to describe any ultrasound transducer array with a curved surface having curvature about two or more axes (e.g., both transverse and longitudinal axes of a rectangular array). Elements of a 3D curved array may be displaced relative to all adjacent elements in three dimensions. Thus, 3D curved arrays may be described as having a 3-dimensional quadric surface shape, such as a paraboloid or a section of a spherical surface. In some cases, the term 3D array may refer to curved CMUT arrays in addition to machined piezoelectric arrays.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a group of transducer elements that are collectively managed as a common group by imaging control electronics. For example, in some embodiments an aperture may be a physical grouping of elements which may be physically separated from elements of an adjacent aperture. However, adjacent apertures need not necessarily be physically separated.

It should be noted that the terms "receive aperture," "insonifying aperture," and/or "transmit aperture" are used herein to mean an individual element, a group of elements within an array, or even entire arrays with in a common housing, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture will all have the same dimensions. In the case of a multiple aperture imaging arrangement, the dimensions of the total aperture includes the sum of the dimensions of all send and receive apertures.

In some embodiments, two apertures may be located adjacent one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Multiple aperture ultrasound imaging techniques can benefit substantially from the physical and logical separation of ultrasound transmitting and receiving functions. In some embodiments, such systems may also substantially benefit from the ability to receive echoes substantially simultaneously at two or more separate receive apertures which may be physically spaced from a transmit aperture. Further benefits may be achieved by using one or more receive apertures located on a different scan plane than elements of a transmit aperture.

Elements and arrays described herein may also be multi-function. That is, the designation of transducer elements or arrays as transmitters in one instance does not preclude their immediate redesignation as receivers in the next instance.

Moreover, embodiments of the control system herein include the capabilities for making such designations electronically based on user inputs, pre-set scan or resolution criteria, or other automatically determined criteria.

In some embodiments, each echo detected at a receive aperture may be stored separately in volatile or non-volatile memory within the imaging electronics. If the echoes detected at a receive aperture are stored separately for each pulse from the insonifying aperture, an entire two-dimensional image can be formed from the information received by as few as just one element. Additional copies of the image can be formed by additional receive apertures collecting data from the same set of insonifying pulses. Ultimately, multiple images can be created substantially simultaneously from one or more apertures and combined to achieve a comprehensive 2D or 3D image.

Multiple Aperture Ultrasound Imaging (MAUI) methods and systems have been previously introduced in Applicants' prior US patent applications referenced above. These applications describe multiple aperture imaging techniques and systems including embodiments which consider each individual receive element as an independent aperture from which a complete 2D image can be formed. Many such receive apertures can form many reconstructions of the same 2D image but with different point spread functions and different noise components. A combination of these images provides a vastly-improved overall image in terms of both lateral resolution and reduction of speckle noise.

As discussed in Applicant's previous applications, in order for the images from multiple receive apertures to be combined coherently, the relative acoustic position of each element relative to the transmit element(s) (or some other fixed coordinate system relative to the probe) must be known precisely to a desired degree of accuracy. Traditionally, the position of transducer elements is typically assumed to correspond to a geometric center of a structure forming an element. For example, in the case of a conventional 1D phased array probe, the mechanical position of the elements may determined by the size of the cuts inside the crystal wafer 110, in FIG. 6B. The acoustic center is generally assumed to be at the center of the shaped crystalline structure; (e.g., a parabolic channel running down the mid portion of the elements, 120, FIG. 6B).

However, the acoustic position of transducer elements may not necessarily correspond exactly to their geometric or mechanical positions. Therefore, in some embodiments, the true acoustic position of each element in an array can be determined by a calibration system and process, as described in Applicants' previous applications.

Substantial imaging and practical use benefits may be achieved by using multiple aperture imaging processes with a concave curved ultrasound transducer array. In some embodiments, a concave transducer array may have a relatively large radius of curvature, as shown for example in FIG. 6. In other embodiments, as shown for example in FIG. 7 a concave transducer array may have a relatively small radius of curvature. In some embodiments, such a concave curvature may be substantially continuous as shown, or a similar concave structure may be formed by joining a plurality of linear segments. With adequate calibration, virtually any array shape may be formed and utilized.

Although the following embodiments are described with reference to a single, continuous transducer array, the skilled artisan will recognize that the same basic structures, features and benefits may be achieved by using a plurality of separate transducer arrays, each of which may have a planar or curved shape as desired. Thus, it is to be appreciated that any number of elements or blocks of arrays may be used in a multiple aperture probe using the systems and methods described herein.

As will be discussed in more detail below, in some embodiments, a concave ultrasound imaging probe may be used in combination with imaging control electronics having a number of unique adjustment and control parameters. For example, by providing a substantially continuous concave curved transducer array in combination with suitable control electronics, the physical location of transmit and/or receive apertures may be changed dynamically without moving the probe. Additionally, the size and number of elements assigned to a transmit and/or receive aperture may be changed dynamically. Such adjustments may allow an operator to adapt a system for a broad range of variations in use and patient physiology.

FIG. 1 illustrates an embodiment of a multiple aperture ultrasound imaging system control panel configured for use with at least one ultrasound imaging array and a control system configured to drive and control ultrasound imaging with the array(s). The control system can be referred herein to as MAUI electronics, and can include such features as a computer processor, memory, a pulse generator, software configured to control any attached ultrasound arrays. The MAUI electronics are illustrated throughout this application, and it should be understood that the various embodiments of ultrasound arrays illustrated herein can each be driven and controlled by MAUI electronics. In some embodiments, a MAUI control panel may include aperture controls such as an aperture view angle control 410 and an aperture width control 420. A MAUI control panel may also include element controls 430 and 440 configured to adjust the number of elements used for each transmit aperture and each receive aperture, respectively. In some embodiments, the controls 410, 420, 430, 440 may include buttons, knobs, scroll wheels, trackballs, touch pads, sliders or any other suitable human interface device.

Figure 2:
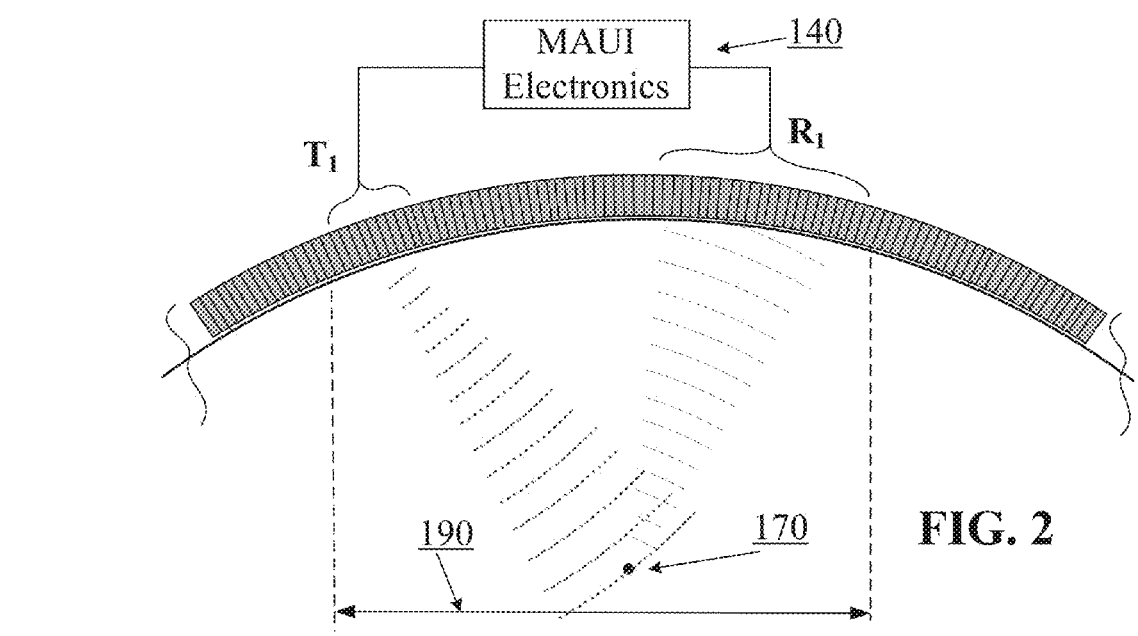
FIG. 2 is a schematic diagram of a concave curvilinear transducer array where various elements are designated as transmit and receive apertures.

FIG. 2 illustrates one embodiment of a concave curvilinear array of ultrasound transducer elements during a single multiple aperture ultrasound imaging cycle. In this illustration, one or more elements in a transmit aperture $T_1$ are shown transmitting energy into a medium. Transmit beamforming may utilize either a phased array or be a simple ping. In either case, energy is transmitted toward region of interest which has at least one reflector 170. Receive aperture elements $R_1$ may be electronically designated to collect data for this transmit cycle by the MAUI Electronics 140.

Based on calibrated acoustic position data defining the position of each element, individual distances of all receive elements in $R_1$ from the element(s) of the transmit aperture $T_1$ for this capture period may be computed in firmware or hardware. This allows data from the receive aperture $R_1$ to be assembled into an aligned image in real time immediately upon receipt. Image compounding or post processing is not required and may be omitted.

The size (e.g., width) of the single aperture of a conventional phased array probe, and hence the resolution, can be severely limited by the variation of speed of sound in the tissue between the transducer and the organ of interest. Although speed of sound in various soft tissues throughout the body can vary by +/−10%, it is usually assumed that the speed of sound is constant in the path between the transducer and the organ of interest. This assumption is valid for narrow transducer arrays in systems using one transducer array (e.g., a single array used for both transmit and receive). However, the constant speed of sound assumption breaks down as the probe's total aperture becomes wider because the ultrasound pulses pass through more tissue and possibly diverse types of tissue. Tissue diversity under the length of the transducer array may affect both the transmit and the receive functions.

When a reflector such as reflector 170 in FIG. 2 is insonified by either a focused pulse from a group of transmit elements or a ping from a single transmit element, the reflector 170 reflects an echo back to all of the elements of a designated receive aperture $R_1$. Coherent addition of images collected by elements in this receive aperture can be effective if the speed of sound variations in the paths from reflector 170 to each of the receiver elements in $R_1$ do not exceed +−180 degrees phase shift relative to one path chosen as reference.

The maximum physical size of the aperture $R_1$ for which coherent addition can be effective is dependent on tissue variation within the patient and cannot be computed accurately in advance. Conventional ultrasound imaging systems are typically designed with an aperture width that is a compromise for a wide range of possible patients, studies and view angles so as to avoid phase conflicts for a wide range of expected uses. However, because they involve compromise, such conventional probes do not necessarily produce an optimum image. Phase coherence is equally important when using a group of elements to generate a focused transmit beam, and again is often a compromise in conventional transducer array widths and operation.

Thus, in some embodiments, the size (e.g., width in terms of number of designated elements) of transmit and/or receive apertures may be controlled either automatically or manually using controls such as the multiple aperture ultrasound imaging system control panel shown in FIG. 1. Adjusting the aperture size may allow the operator to find the best aperture for each individual patient. In alternative embodiments, an optimum aperture size may be found automatically by programming the control electronics to rapidly try several array sizes and pick the one yielding best image acuity (e.g., sharpness, high frequency content). Thus, in some embodiments, a control panel may include button or other control to initiate such an automatic aperture-size-determination procedure. In some embodiments, such aperture size adjustments may be applied to a total aperture size for a probe or application. Alternatively or in addition, such aperture size adjustments may be applied to individual transmit or receive apertures.

An optimum receive aperture size for a particular patient or application may be determined electronically or controlled manually. The optimum aperture is the aperture size that retains the best signal to noise ratio while still in phase. An aperture that is too wide will lose one or both of these qualities, and degrade the image. Therefore in some embodiments, the sonographer may control the size of the group of receiver elements used for each receiver group $R_1$ in FIG. 2 by manipulating controls 410, 420, 430 and 440 until he/she sees no further improvement in image quality. In another embodiment, a controller in the MAUI electronics 140 can be configured to automatically select the size of the group of receiver elements used for receiver group $R_1$ by determining the best signal to noise ratio while still in phase.

The size of the group of transmitter elements $T_1$ depends on whether the transmitted pulse is a focused beam formed from the phased firing of a group of transducer elements or an unfocused pulse from just one or a few elements at a time. In the first case, the transmit aperture size may be limited to the same size as the optimum receive aperture size. In embodiments using unfocused pings, the transmit aperture size is much less critical since variation in the path time from transmitter elements to a reflector such as 170 will change only the displayed position of the point corresponding to the reflector 170. For example, a variation resulting in a phase shift of 180 degrees in the receive paths results in complete phase cancellation, whereas the same variation on the transmit paths results in a displayed position error of only a half wavelength (typically 0.2 mm), a distortion that would typically not be noticed.

Thus, with continued reference to FIG. 2, the speed of sound along the paths from element(s) of the transmit aperture $T_1$ to the reflector 170 need not be accounted for in the coherent addition of the received signals. The aperture size of the receiver group $R_1$, on the other hand, may be as large as for a conventional phased array (e.g., about 2 cm) in some embodiments. But unlike a conventional array, the total aperture 190 (e.g., the maximum distance from the furthest-left transmit element of $T_1$ to the furthest-right receive element of $R_1$ in the FIG. 2 embodiment) determining the lateral resolution of the system is much larger.

A single image can be formed by coherent averaging of all of the signals arriving at the receiver elements as a result of a single insonifying ping. Summation of these images resulting from multiple pings may be accomplished either by coherent addition, incoherent addition, or a combination of coherent addition by groups and incoherent addition of the images from the groups. Coherent addition (retaining the phase information before addition) maximizes resolution whereas Incoherent addition (using the magnitude of the signals and not the phase) minimizes the effects of registration errors and averages out speckle noise. Some combination of the two modes is probably best. Coherent addition can be used to average ping images resulting from transmit elements that are close together and therefore producing pulses transmitted through very similar tissue layers. Incoherent addition can then be used where phase cancellation would be a problem. In the extreme case of transmission time variation due to speed of sound variations, 2D image correlation can be used to align ping images prior to addition.

The wide aperture achieved by separating the transmit and receive apertures is what allows for the higher resolution imaging associated with Multiple Aperture Ultrasound Imaging (MAUI). However, this wide aperture does not by itself reduce another significant detractor of ultrasound imaging; speckle noise.

Speckle noise patterns are associated with the transmit source. That is, during receive beamforming, the speckle noise pattern from a steady state phased array or ping transmit source appear as constant "snow" in the displayed image as long as the probe or tissue being imaged is not turned or moved significantly during imaging. If the probe is moved or twisted, the speckle noise or "snow" on the image will obscure a new portion of the image. Hence, data collected at a single receive aperture from transmissions from alternate transmit apertures will subsequently have many different speckle noise patterns.

Figure 2A:
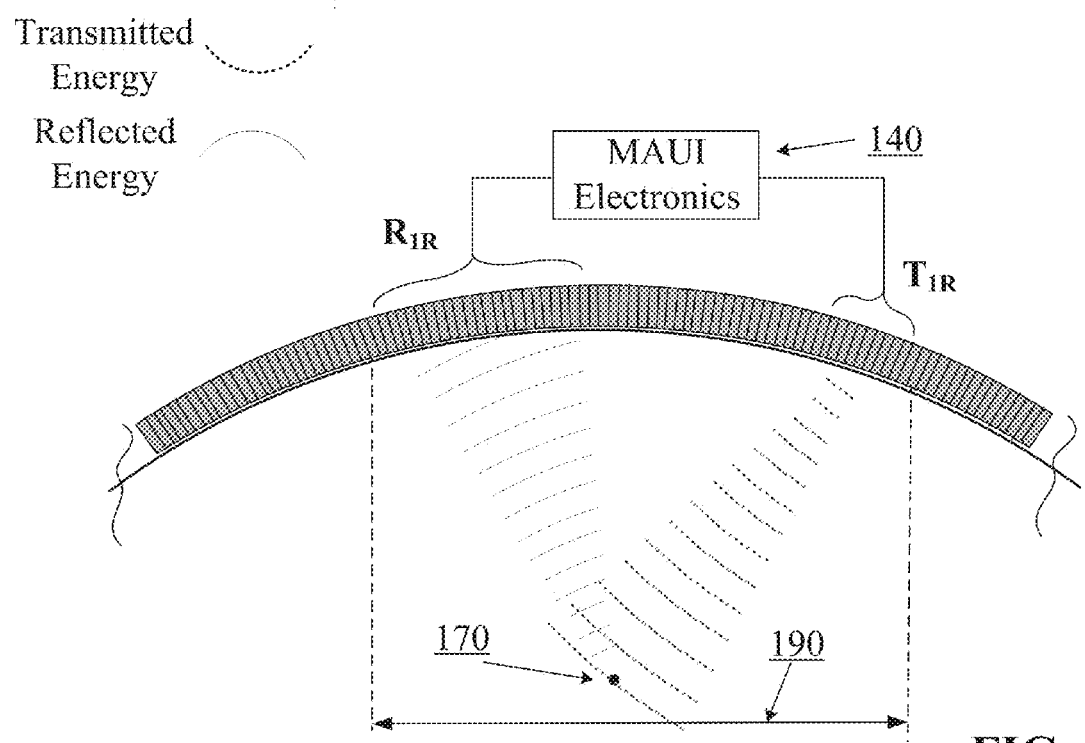
FIG. 2A is a schematic diagram of a concave curvilinear transducer array where elements are put to use in the reciprocal transmit or receive function relative to FIG. 2.

In the embodiment illustrated in FIG. 2 data collected at receive aperture $R_1$ is coming from a single transmit source $T_1$, and therefore will have a singular consistent speckle noise pattern. By itself, this is the same limiting factor of conventional ultrasound today. However, by initiating a second insonification from the reciprocal positions $T_{1R}$ and $R_{1R}$ of FIG. 2A upon the completion of the first image capture, a second image may be obtained almost immediately. This second image (from transmit source $T_{1R}$) will have a different speckle noise pattern than the first (from transmit source $T_1$). Thus, by combining the two images, both speckle noise patterns may be substantially identified and eliminated. The ability to invert the roles of transmitter and receiver in array elements produces differing noise patterns which will substantially cancel each other out once combined. The result of this array role reversal is a much clearer ultrasound image while still maintaining the same high resolution from the wider total aperture 190.

Figure 2B:
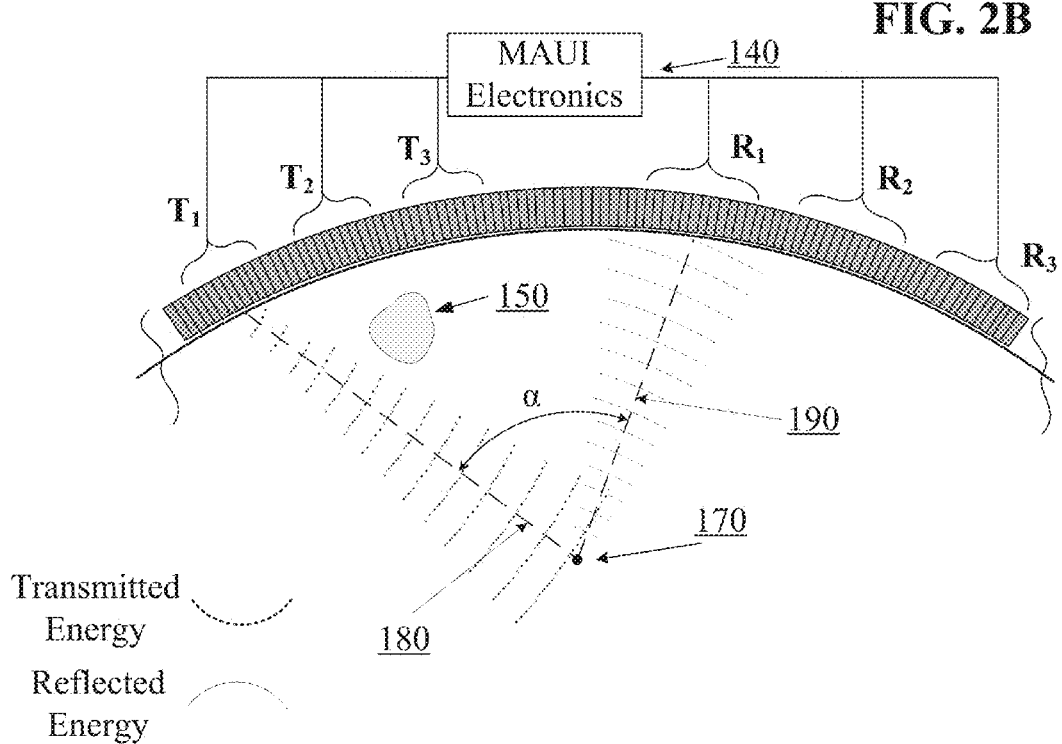
FIG. 2B is a schematic diagram of an embodiment of a concave curvilinear transducer array where elements of transmit and receive apertures are predesignated to insonify each other in rapid succession using like sized apertures.

FIG. 2B demonstrates an embodiment in which a concave curved multiple aperture array cycles through a number of different views of the region of interest 170. The advantage of this process is to gain sequential images of the same target and then combine the images for a more comprehensive presentation to the sonographer. In this case, the MAUI Electronics 140 may simply cycle through a programmable sequence of transmit and receive apertures across the entire width of the array or collective arrays while maintaining a fixed maximum total aperture width.

In some embodiments, an array of this type may be configured to include transmit and receive elements with different frequency ranges interspersed in the array. As an example, $T_1$ and $R_1$ could be tuned to 2 MHz, $T_2$ and $R_2$ could be tuned to 5 MHz, and $T_3$ and $R_3$ could be tuned to 10 MHz. This technique would further reduce speckle noise in the images.

FIG. 2B also demonstrates another unique feature of some embodiments of multiple aperture arrays called view angle control. The view angle may be defined as the angle α between lines 180 and 190 that could be drawn from $T_1$ to 170 and from $R_1$ to 170. In some embodiments, the MAUI electronics 140 may be configured to automatically move the transmit T1 and receive R1 apertures along the array or arrays without changing the total distance between the transmit $T_1$ and receive $R_1$ apertures. In other embodiments, the transmit and receive apertures can be moved manually, such as with the view angle control 410 of FIG. 1.

In some embodiments, further improvements of the images can sometimes be obtained by rapidly changing the positions of the groups (including switching the designations of the groups relative to transmit and receive functions) and adding the resulting images incoherently.

An array placed near a physiology that creates an obstruction (e.g., a vertebrae, rib, wrist bone, etc.) would not be able to combine or compound a complete image. With a conventional probe, a sonographer would physically move the probe on the patient's skin to obtain a clear ultrasound window. However, with a dynamic multiple aperture ultrasound probe, the view angle of the probe can be adjusted to compensate for an obstruction in the field of view. For example, if the view created by $T_2$ and $R_2$ is obstructed by a bone or other obstruction 150, then the MAUI electronics 140 can automatically rotate that view angle over to $T_1$ and $R_1$, or alternatively to $T_3$ and $R_3$, until the region of interest is un-obscured. In other embodiments, this technique can be performed manually by a sonographer.

Figure 2C:
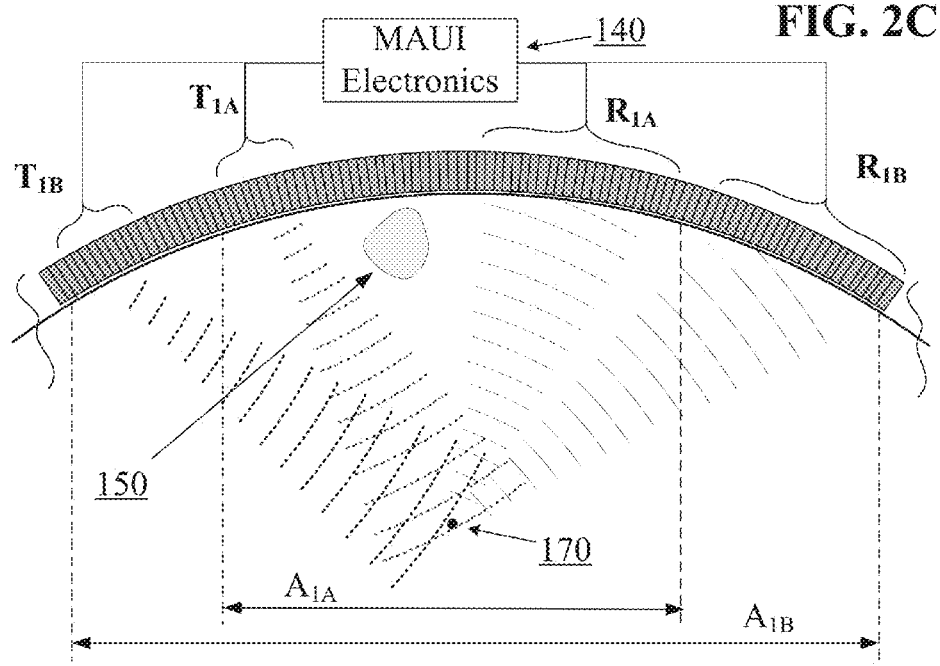
FIG. 2C is a schematic diagram of an embodiment of a concave curvilinear transducer array demonstrating how transmit and receive apertures can be widened around a desired view angle to achieve greater resolution of the target area.

FIG. 2C illustrates another important capability of some embodiments of multiple aperture arrays, referred to herein as total aperture size control. In this embodiment, the view angle created by $T_{1A}$ and $R_{1A}$ provides an obstruction-free view of the region of interest including reflector 170 which avoids obstruction 150. In this example, the system is providing multiple aperture imaging with a total aperture width of $A_{1A}$. Using total aperture size control, the total aperture width can be varied either inward or outward on the array, while maintaining a fixed view angle center. Thus, in some embodiments, as a total aperture size is adjusted, both transmit and receive apertures may be electronically moved at the same rate outward or inward from the fixed view angle center so as to maintain the original view angle.

Radian resolution is proportional to λ/d, where λ is wavelength and d is total aperture width. The wider the total aperture, the higher the resolution; the smaller the total aperture, the lower the resolution. The total aperture width can be varied to get the best possible resolution for a chosen view angle. For example, in the embodiment of FIG. 2C, the total aperture width can be maximized by selecting the total aperture width between $T_{1B}$ and $R_{1B}$, resulting in a total aperture width of $A_{1B}$.

Figure 3:
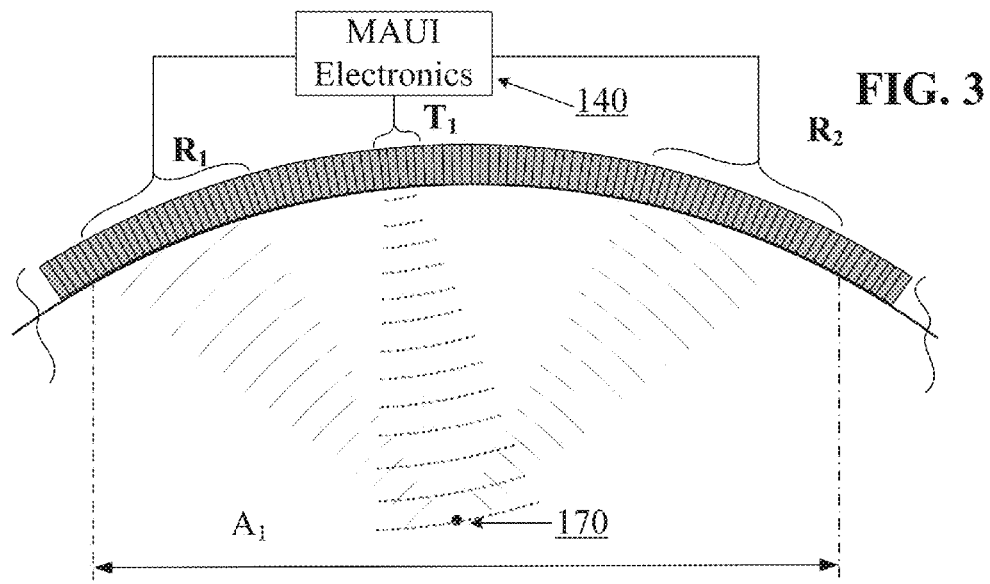
FIG. 3 is a schematic diagram of an embodiment of a concave curvilinear transducer array illustrating a pulse transmitted by a single designated transmit aperture and being received by multiple designated receive apertures.
Figure 3A:
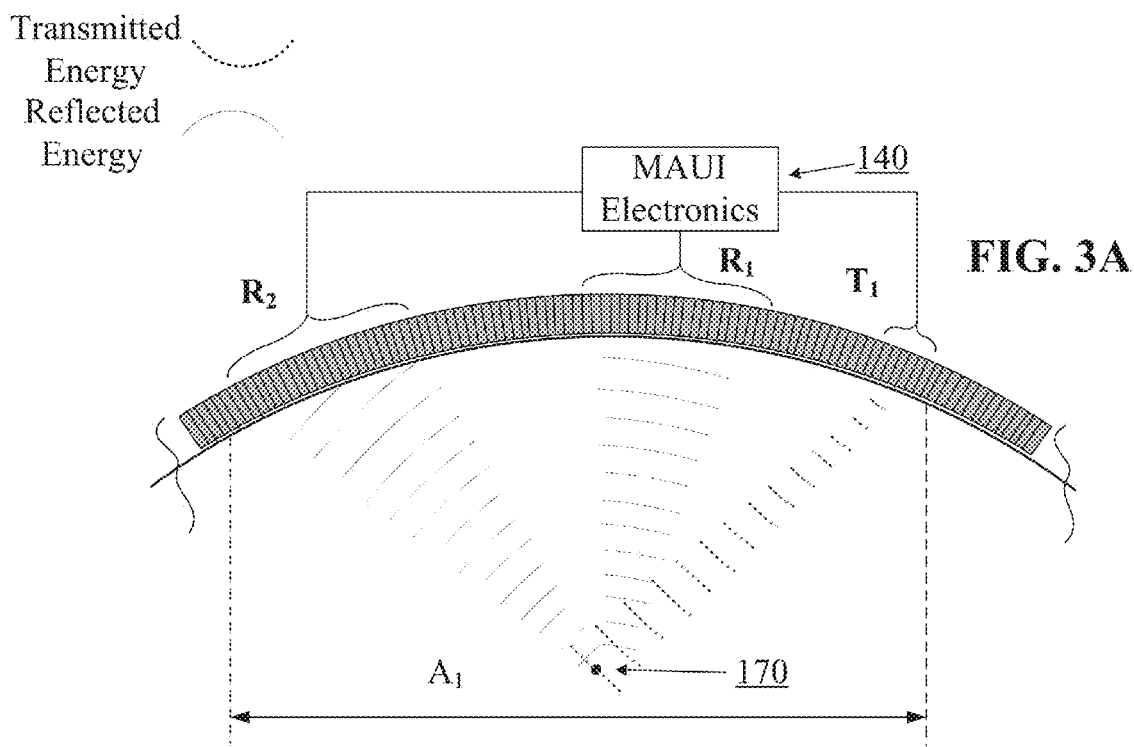
FIG. 3A is a schematic diagram of an embodiment of a concave curvilinear transducer array where the transmit aperture and multiple receive apertures can be electronically controlled to operate in different positions.

In additional embodiments, data may be collected at multiple receive apertures for a single transmit pulse, as illustrated in FIGS. 3 and 3A. Data collection in this fashion provides the added benefit of increased aperture width $A_1$ during real time data collection.

In FIG. 3, total aperture width $A_1$ is determined by the distance between the outer most elements of receive apertures $R_1$ and $R_2$. In FIG. 3A, the total aperture width $A_1$ is determined by the distance between the outer most elements of transmit aperture $T_1$ and receive aperture $R_2$. Since multiple apertures are being used in the receive beamformer simultaneously, higher resolution can be attained in real time. This capability allows for precise data capture on moving objects, like coronary valves.

However, unlike embodiments using only a single receive aperture, multiple receive aperture beamforming often requires a speed of sound correction to accommodate differing tissue attenuation speeds situated along multiple "lines of sight" to the region of interest (e.g., referring to FIGS. 3 and 3A, a first line of sight being from reflector 170 to $R_1$, and a second line of sight being from reflector 170 to $R_2$). This calculation should be made if data collected nearly simultaneously from different receive apertures is to be coherently combined. Embodiments of techniques and methods for such speed of sound corrections are described in Applicants' prior patent applications referenced above.

The examples in FIGS. 2-3A demonstrate embodiments of multiple aperture imaging using a multiple aperture array or arrays with elements that are aligned within the same scan plan. Such arrays may be 1D, 1.5D, or 2D or CMUT concave curved arrays. 3D volumes can be constructed by piecing together 2D slices generated using such systems into a 3D volume. This is a post processing function, so data from a 1D multiple aperture array cannot image 3D data in real time (also known as 4D imaging).

Embodiments of concave curved arrays of 1.5D, 2D, 3D and CMUT transducer arrays have more capabilities which will now be examined. Such arrays may have concave curvature about one or two or more axes. Although many of the following embodiments are described with reference to arrays having curvature about two axes, similar methods may be applied using transducer arrays having curvature about only one axis.

Figure 4:
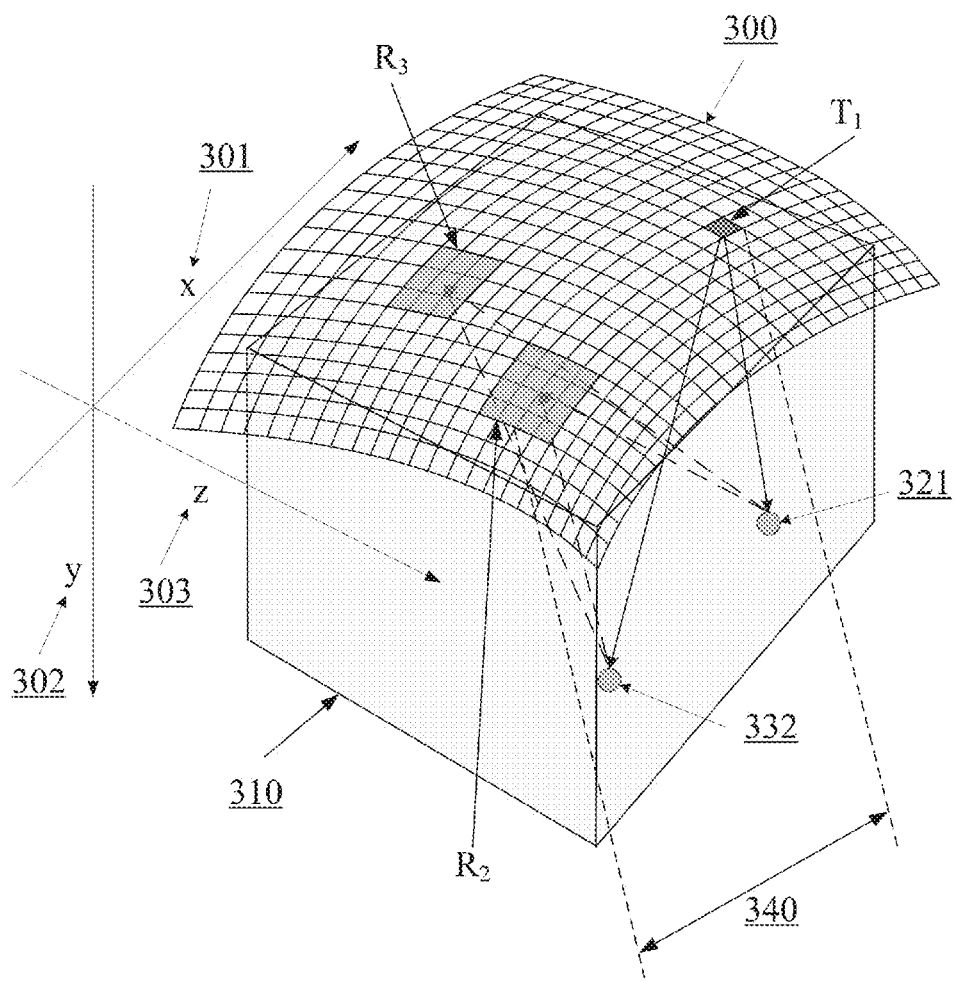
FIG. 4 is a schematic diagram of an embodiment a concave curvilinear matrix with curvature in two orthogonal directions, also referred to as a Three Dimensional (3D) array. Each element in a 3D array is displaced relative to adjacent elements in all of x, y, and z axes. In this illustration, an element or elements of a transmit aperture is designated to insonify the medium. Multiple targets in the medium are illustrated for the purpose of demonstrating how volumetric data may be gathered. Multiple receive apertures are illustrated to demonstrated how simultaneous gathering of data may involve timing and tissue speed of sound adjustments.

FIG. 4 illustrates a concave 3D transducer array 300 having curvature about two orthogonal axes. In some embodiments, a 3D concave curved array 300 may be constructed using machined piezoelectric transducers. In other embodiments, the array 300 may be constructed using CMUT transducers such as those illustrated in FIG. 6C, 7E or 8E. Calibration of a 3D array may be needed as each element of the array will have slightly different positions in the x axis 301, y axis 302 and z axis 303.

In some embodiments, calibration data including element position information may be stored in a calibration chip onboard each MAUI probe so that it can be used by MAUI electronics during processing. In other embodiments, calibration data including element position information may be stored in a remote database which may be accessed electronically by communications components within the probe or within an ultrasound imaging system. For example, calibration data may be stored in an Internet-accessible database which may be accessed by an ultrasound imaging system. In such embodiments, the probe may include a chip storing a unique identifier which may be associated with corresponding calibration data in a remote database.

In the illustration of FIG. 4, a snap shot of multiple aperture data collection is depicted en route to building an image of an entire volume 310. Here, an element or elements of a transmit aperture $T_1$ transmit a pulse into the volume that includes scatterers such as 321 and 322. The elements making up receive aperture $R_2$ may be assembled in a variety of shapes. Here, a square of elements makes up the receive apertures $R_2$ and $R_3$. As mentioned above, the speed of sound along the path from the transmit aperture $T_1$ to the reflector 321 or 322 is irrelevant to the coherent addition of the received signals as long as a single aperture is used to receive, however, speed of sound corrections can be made to improve image quality when using multiple receive apertures $R_1$ and $R_2$.

In some embodiments, the size of the receive aperture $R_2$ may be as large as for a conventional phased array (e.g., about 2 cm). But unlike a conventional array, the total aperture 340 determining the lateral and transverse resolution of the system is much larger comprising the distance from the transmitter $T_1$ to the group of receiver elements $R_2$, and could be as wide as the entire array 300 or wider if a transmitter was located on another array within the probe (or in a separate probe in electronic communication). The elements located in the receive aperture $R_2$ each collect volumetric data from the $T_1$ transmit pulse. Since a speed of sound correction is not required for data collected from a single transmit pulse at a single aperture, data from each element of $R_2$ may be coherently averaged with the other elements in pre-processing.

A speed of sound correction may or may not be required for averaging volume renderings for multiple pulses depending on the size of the transmit aperture (i.e., a total distance between furthest elements of a transmit aperture). If the transmit aperture is small enough that the transmit elements transmit through substantially the same types of tissue, coherent addition may still be possible. If the transmit aperture is larger, a speed of sound correction in the form of incoherent addition may be required.

If the transmit aperture is large enough that the transmit elements are still farther apart, the correction may take the form of incoherent addition of echoes received at each element, but alignment may be accomplished by cross correlation or some form of adjustment to maximize acuity, such as adjustment of the view angle, individual aperture size and/or total aperture size. A 3D concave array may provide mechanically better view angles of a region of interest than conventional coplanar 2D arrays because of its concave curvature and width.

In some embodiments, a 3D array may also image tissues of varying density. FIG. 4 illustrates a second receive $R_3$ aperture that can be used simultaneously with $R_2$ during a single transmit pulse from a transmit aperture $T_1$. However, unlike the single receive aperture situation, multiple receive aperture beamforming may require a speed of sound correction to accommodate differing tissue attenuation speeds situated along multiple "lines of sight" to the region of interest.

In this case, the elements located in aperture $R_3$ may collect volumetric data from the $T_1$ transmit pulse. Again, since a speed of sound correction is not required for echoes received by multiple elements of the single receive aperture $R_3$, data from each element in $R_3$ may be coherently averaged with the other elements of $R_3$ in pre-processing.

Volumes for $R_2$ and $R_3$ may be stored in memory and may then be incoherently averaged with one another to create a single 3D volume. While only receive apertures $R_2$ and $R_3$ are illustrated here, any number of receive apertures can be used. In some embodiments, receive apertures may use the entire array 300 as a total aperture. Using multiple receive apertures greatly reduces noise as well as increases total aperture size to provide higher resolution.

Figure 4A:
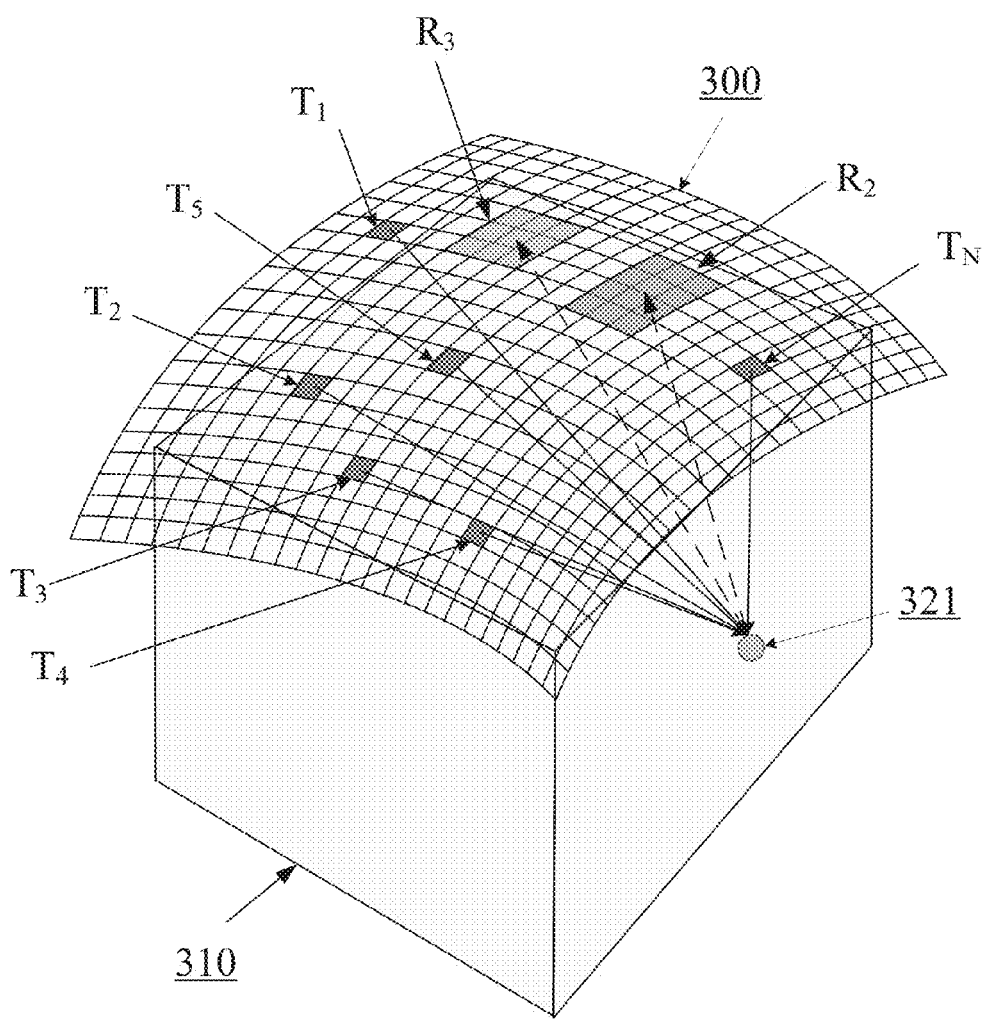
FIG. 4A schematically illustrates an embodiment of a 3D array. Multiple transmit apertures $T_1$ through $T_N$ are indicated for the purpose of demonstrating transmit pulses being received on one or more receive apertures $R_2$ and/or $R_3$. A single target is indicated for the purpose of demonstrating how data may be gathered.

Like 2D multiple aperture imaging, the 3D multiple aperture imaging made possible by a 3D concave curved array may use many transmit apertures. Even with a 3D array, the noise patterns associated with $T_1$ will have a singular consistent speckle noise pattern. FIG. 4A demonstrates transmit pulses from multiple apertures $T_1$ through $T_N$. In the illustrated case, alternate transmit locations may be utilized, but only a single receive aperture $R_2$ is used so speed of sound corrections are not needed. Data collected at $R_2$ can be coherently averaged for each element in that receive aperture and subsequently for each transmit pulse, and finally placed into memory. Once all transmit pulses are completed, volumetric data may be incoherently combined. Data from the differing transmit elements will produce differing noise patterns that will cancel each other out once combined to provide a much clearer 3D ultrasound image.

Figure 4B:
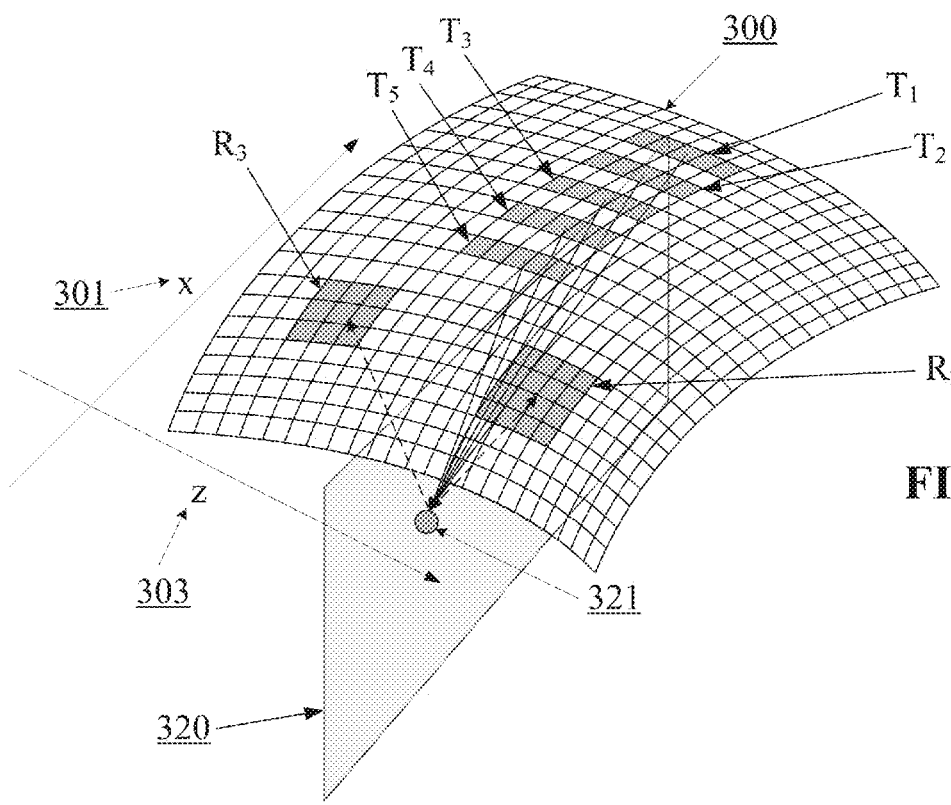
FIG. 4B schematically illustrates an embodiment of a 3D array being used to collect data for a 2D longitudinal slice along the x axis. In this instance, a line of elements in the transverse axis z are being used to form transmit aperture $T_1$. Data along the longitudinal slice may be collected by elements located in receive aperture $R_2$. Multiple transmit apertures, identified as $T_1$ through $T_5$ that can be used along the length of the longitudinal slice to assist in data collection over time. Another receive aperture $R_3$ is indicated that can be used to collect either simultaneous data for the same transverse slice, or separate data for a different longitudinal slice.

FIGS. 4B and 4C illustrate a 3D array being using to collect a 2D slice of data. In the case of FIG. 4B, the slice 320 is along the longitudinal axis of the array. In the case of FIG. 4C, the slice 330 is along the transverse axis of the array. 2D slices may also be obtained at any other angle relative to the probe. In some embodiments, the probe may use a partial line of elements to create transmit aperture $T_1$. In some embodiments, elements may be energized in phase to focus a beam onto the plane 320 in FIG. 4B or the plane 330 in FIG. 4C. In these cases, the elements of $T_1$ may be narrow so that the energy is unfocused in the direction of the plane. The length of the partial line of elements in $T_1$ may be chosen to be long enough to focus the width of the plane.

Referring again to FIGS. 4B and 4C, receive aperture $R_2$ can be used singularly to collect data for longitudinal slice 320. The elements located in aperture $R_2$ each collect data from the $T_1$ transmit pulse. Since a speed of sound correction is not required for this type of collection, data from each element may be coherently averaged with the other elements in pre-processing. Subsequently, transmitter groups $T_1$, $T_2 \ldots T_N$ may each be fired to insonify the plane 320 (or 330), each with a different x (or z) position. Partial images of the plane may then be combined either coherently or incoherently with the same considerations as discussed with respect to the embodiments discussed above with reference to FIGS. 2 and 3.

As discussed above, the view angle and total aperture width can be adjusted. In some embodiments, the view angle may be adjusted in any desired direction along the 3D array.

With a 3D concave array, a 2D slice angle adjustment may also be provided to allow for selection of a 2D slice to be imaged without having to rotate a probe. A 2D slice angle adjustment may effectively allow rotation of a 2D slice around the y axis to obtain a 2D slice at any angle between that of FIG. 4B and that of FIG. 4C. Similar adjustment may also be provided to allow for a selected 2D slice to be rotated about the x or z axes.

Thus, the arrays described herein may provide an enormous range of flexibility in selecting and optimizing a 2D image without necessarily moving the probe at all. A 3D array provides mechanically better view angles of the region of interest than conventional coplanar 2D arrays because of its concave curvature and greater total width.

Figure 4E:
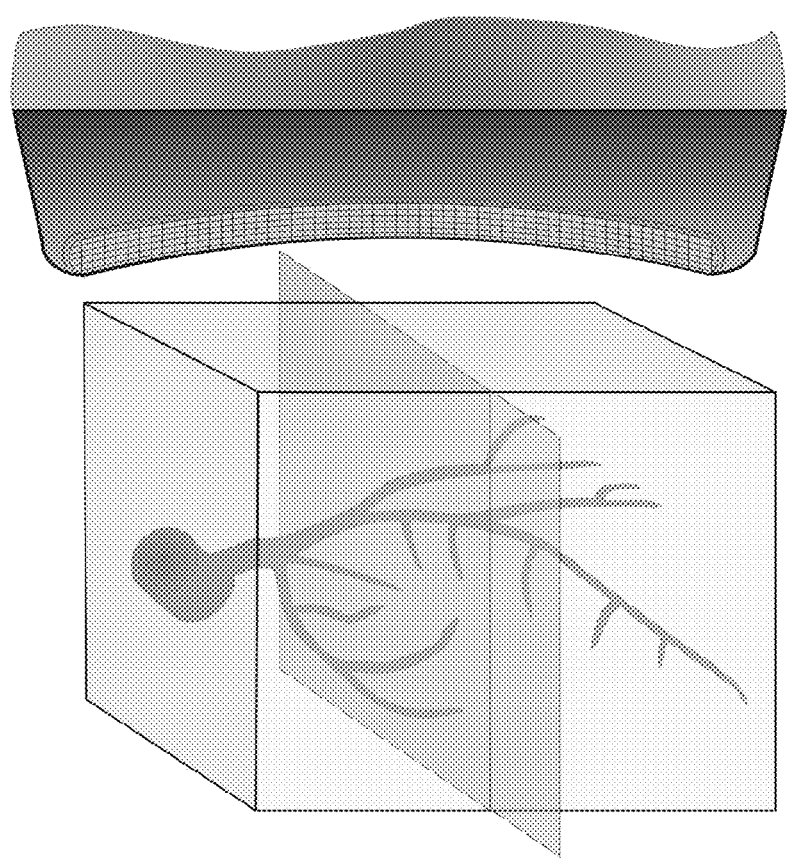
FIG. 4E illustrates a data volume with a 2D transverse slice of data highlighted within the volume. This illustrates a capability of multiple aperture imaging to interchange volumetric 3D/4D imaging with higher resolution 2D imaging in near real time to allow for simultaneous presentation on a display.

FIGS. 4D and 4E demonstrate embodiments of a 3D curved array being used for data collection of 3D volumetric data, alternating with a 2D high resolution slice. The sonographer can use a 3D display containing a selectable 2D longitudinal and axial reference line. When in the side-by-side display mode, the 3D image can show the entire volume, and a multiple aperture 2D image can display a high resolution slice for the reference line selected. This is made possible by the array being able to switch between ping transmit from individual elements for volumetric imaging to a shaped pulse transmit (either longitudinally or axially) for 2D slice data for a desired axis. The 2D slice data receives the benefit of concentrated multiple aperture receiving beamforming on a single slice.

Several embodiments of multi-aperture arrays and their unique transducer housings are described below with reference to FIGS. 5-8E. These examples represent some of the flexibility in ultrasound probe design and fabrication that may be achieved when using multi-aperture techniques. The following embodiments provide examples of some general classes of probes (e.g., concave arrays, 3D arrays, conformal and adjustable arrays); however, because of the flexibility in array configuration, a multiple aperture array allows for many conceivable probes to be constructed that are not illustrated here.

Figure 5A:
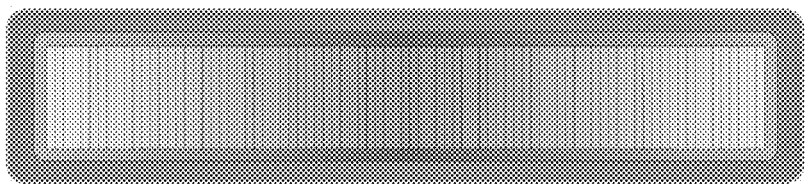
FIG. 5A is a bottom view of an embodiment of a curvilinear array (e.g., 1D, 1.5D or 2D) in a probe such as that shown in FIG. 5.
Figure 5B:
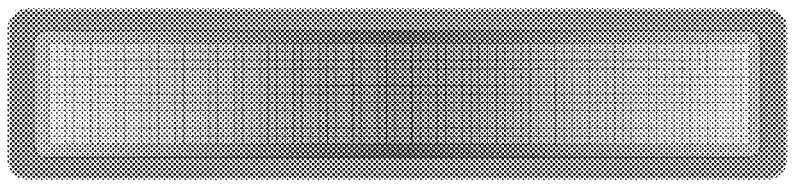
FIG. 5B is a bottom view of an embodiment of a matrix array (e.g., 2D or 3D) in a probe such as that shown in FIG. 5.
Figure 5C:
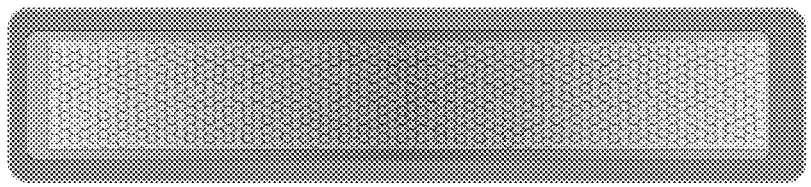
FIG. 5C is a bottom view of an embodiment of a CMUT array in a probe such as that shown in FIG. 5.

FIG. 5 illustrates one embodiment of a general radiology ultrasound probe with a continuous concave curved transducer array. This probe may be operated according to any of the methods described herein. The radius of curvature of this array may be selected to be sufficiently shallow to allow for imaging a variety of body tissues (e.g., abdomen, pelvis, peripheries, etc.). In some embodiments, the concave probe of FIG. 5 may be used to image in 2D as a curvilinear probe using a 1D array such as that shown in FIG. 5A. The probe of FIG. 5 may also operate in 3D or 4D imaging modalities using a 3D piezoelectric array such as that shown in FIG. 5B or a CMUT array such as that illustrated in FIG. 5C.

In some embodiments, a concave array such as that shown in FIG. 5 may be substantially rigidly mounted in a probe. Such an array may be held in place by a backing plate 508. In some embodiments, a single flex connector 505 may be used to electronically connect elements of the transducer array to a cable to be connected to an ultrasound imaging system. In some embodiments, a concave array probe may also include a transmit synchronizer module 502 and probe position displacement sensor 503. In some embodiments, a transmit synchronization module 502 may be used for identifying the start of a transmit pulse when the probe is used as an add-on device with a host machine transmitting. A probe displacement sensor 503 may be an accelerometer, gyroscope or other motion-sensitive device that senses movement of the probe.

A Calibration Chip 501 may also be provided within the probe. In some embodiments, a calibration chip 501 may store calibration data describing the acoustic position of each transducer element as determined during a probe calibration process. In some embodiments, the calibration chip 501 may include non-volatile memory for storing such calibration data. The calibration chip 501 or another component within the probe may also include communication electronics configured to transmit calibration data to an ultrasound imaging system.

Figure 6:
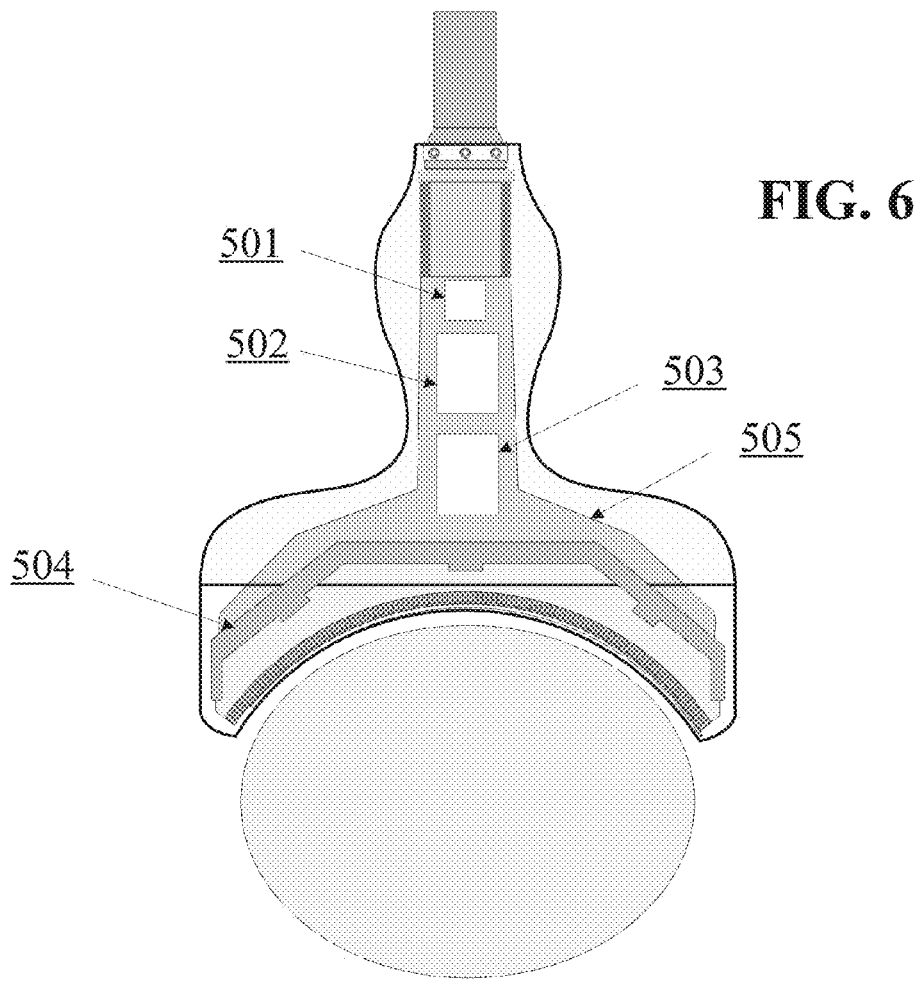
FIG. 6 is a schematic view showing an embodiment of a concave curvilinear probe over a medium of tissue with relatively small radius curvature (e.g., arm, leg, neck, wrist, ankle, etc.).
Figure 6A:
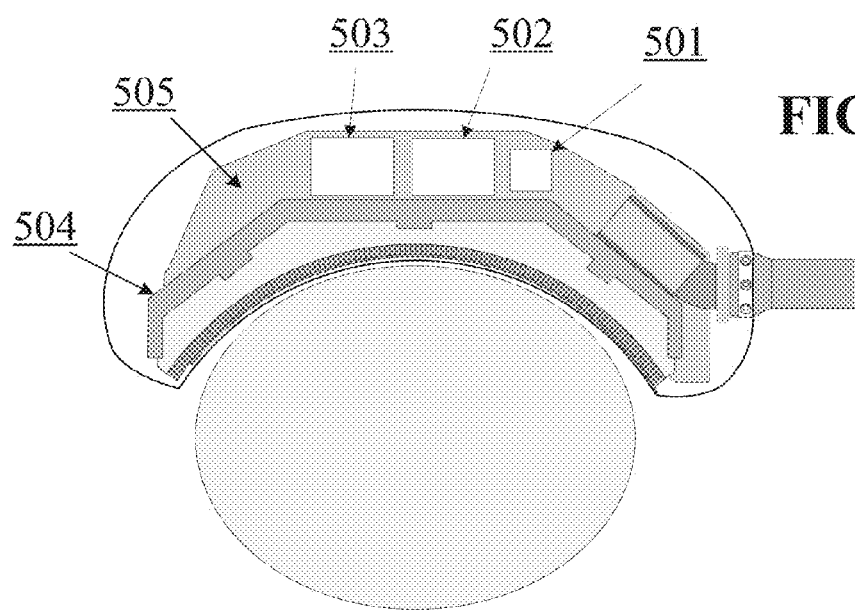
FIG. 6A is a schematic view of an embodiment of a concave curvilinear array similar to that of FIG. 6, but in a probe housing with flex connections that allow for cable connections to be made on the side of the probe housing.

FIG. 6 is another embodiment of an ultrasound probe with a concave array having significantly smaller radius of curvature than the probe of FIG. 5. In some embodiments, the probe of FIG. 6 may be sized and configured to partially surround a joint or extremity. In some embodiments, the curvature of this array may allow a sonographer to image structures behind bone or other obstructions as discussed above with reference to FIGS. 2B and 2C. Similarly, the probe of FIG. 6 may be used to isolate areas of interest by manually or automatically adjusting the position and/or size of transmit and/or receive apertures without moving the entire probe.

Figure 6B:
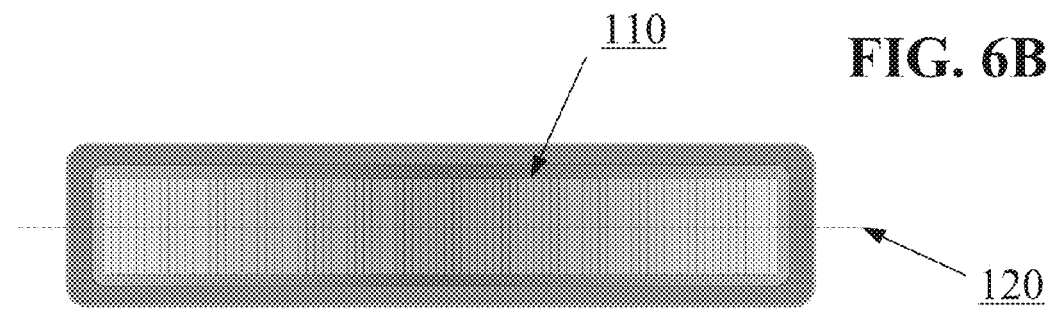
FIG. 6B is a bottom view of an embodiment of a curvilinear array (e.g., 1D, 1.5D or 2D) in a probe such as those shown in FIGS. 6 and 6A.
Figure 6C:
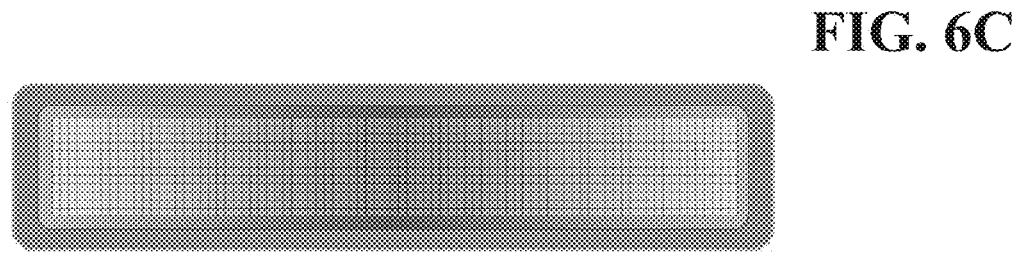
FIG. 6C is a bottom view of an embodiment of a curved matrix (e.g., 2D or 3D) array in a probe such as those shown in FIGS. 6 and 6A.
Figure 6D:
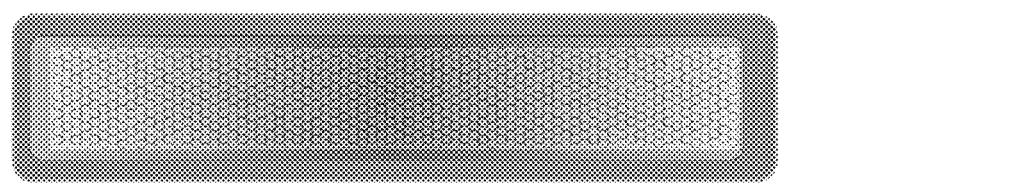
FIG. 6D is a bottom view of an embodiment of a CMUT array in a probe such as those shown in FIGS. 6 and 6A.

In some embodiments, the concave array probe of FIG. 6 may be used to image in 2D as a curvilinear probe using a 1D array such as that shown in FIG. 6B. The probe can also operate in 3D or 4D imaging modalities using a 3D piezoelectric array such as that illustrated in FIG. 6C or a CMUT array such as that illustrated in FIG. 6D. Using methods described herein, the probe of FIG. 6 may be used to produce a complete 3D tomographic display of an extremity or joint while a sonographer holds the probe in one position. Such functionality is not possible with conventional ultrasound imaging arrays. In contrast, a conventional array must be moved around the joint, and images taken from a variety of view angles must be compounded together for a 3D presentation. Because of the incongruences of imaging with a coplanar array and manual movement, a tomographic 3D display from a conventional array is typically not physiologically contiguous.

In some embodiment, the probe of FIG. 6 may be constructed substantially similarly to the probe of FIG. 5. For example, the transducer array(s) may be rigidly mounted to the probe and held in place by a backing plate 508, and may include a flex connector 505. FIG. 6A illustrates an embodiment of a bracelet multiple aperture probe, which may be substantially similar to the probe of FIG. 6, except that the cable connector exits from a side or bottom section of the probe housing. The embodiments of FIGS. 6 and 6A may also include transmit synchronizer modules 502, probe position displacement sensors 503, Calibration Chips 501 and other features discussed elsewhere herein.

Figure 7:
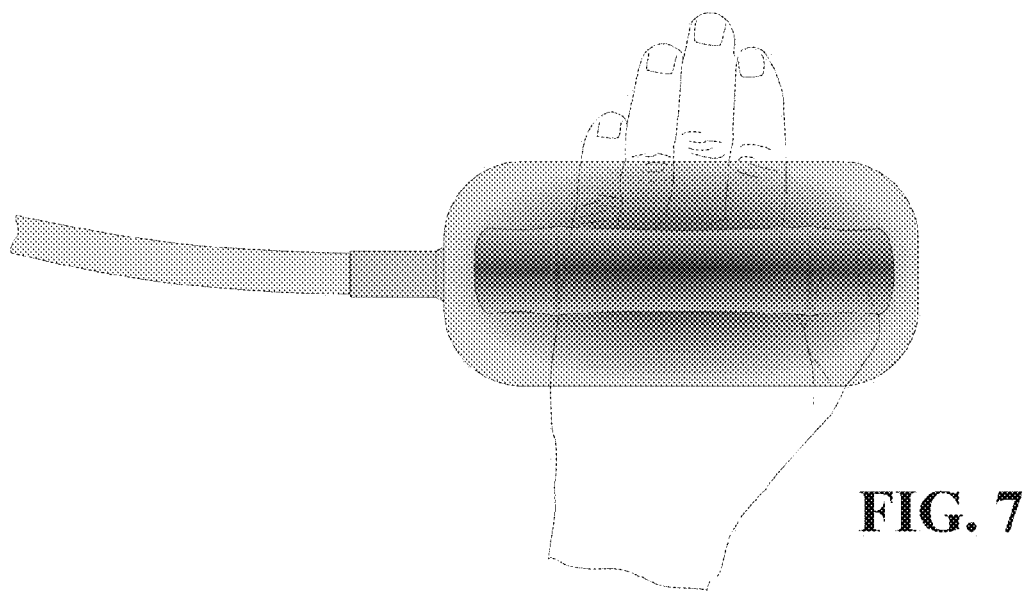
FIG. 7 is a plan view of a concave transducer housing of an embodiment of the probe of FIG. 6A with an adjustable handle aligned with the longitudinal axis of the array.
Figure 7A:
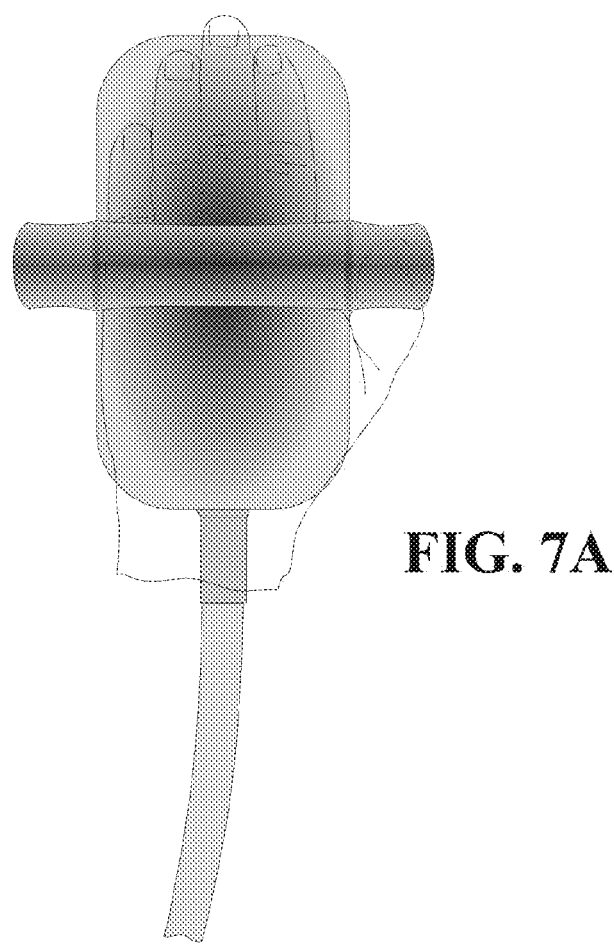
FIG. 7A is a plan view of a concave transducer housing of an embodiment of the probe of FIG. 6A with an adjustable handle aligned with the transverse axis of the array.
Figure 7B:
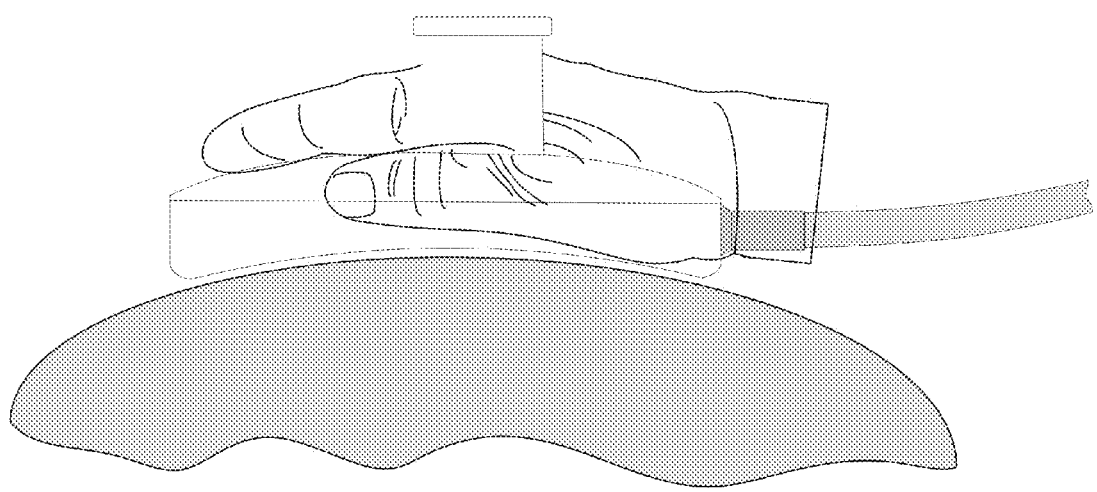
FIG. 7B is a side schematic view showing a concave curvilinear probe of FIG. 7A over a medium of tissue with a relatively large-radius curvature (e.g., abdomen, pelvis, etc.).

FIG. 7 illustrates an embodiment of a general radiology probe configured to fit into the palm of a sonographer's hand. The probe of FIG. 7 may include a curved array such as those shown in FIGS. 5 and 6. The probe of FIG. 7 is made possible by the ability to construct and calibrate a concave ultrasound transducer array. Probes such as this may significantly reduce ergonomic strain on sonographers. The probe of FIG. 7 may also be constructed with a substantially limited elevation or thickness (e.g., as shown in FIG. 7B). Such reduced thickness may allow a sonographer to reach in behind or underneath patients that cannot be moved and still achieve an image over the areas of interest.

In some embodiments, the probe of FIG. 7 may include an adjustable hand support for either right or left handed use. In some embodiments, the hand support may be configured to rotate relative to the probe body to allow the sonographer more flexibility. For example, FIG. 7 illustrates the probe with the hand support in a longitudinal orientation, and FIGS. 7A and 7B show the probe with the hand support rotated to a transverse position.

Figure 7C:
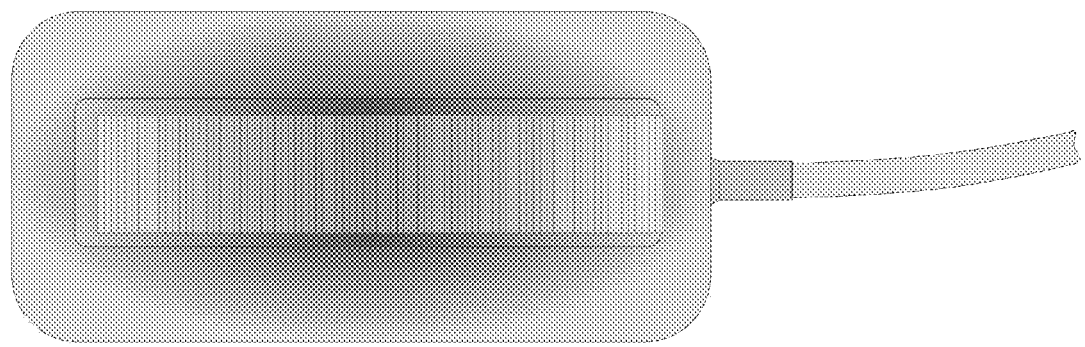
FIG. 7C is a bottom view of a curvilinear array (e.g., 1D, 1.5D or 2D) available for use with the probe styles illustrated in FIGS. 7A-7B.
Figure 7D:
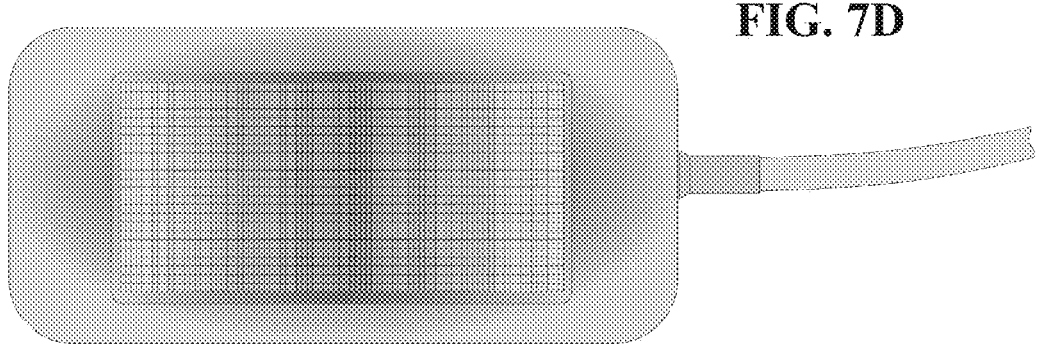
FIG. 7D is a bottom view of a matrix array (e.g., 2D or 3D) available for use with the probe styles illustrated in FIGS. 7A-7B.
Figure 7E:
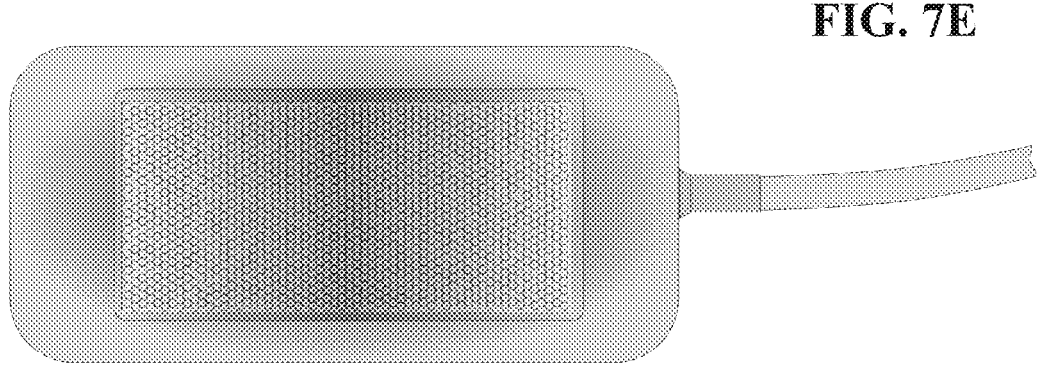
FIG. 7E is a bottom view of a CMUT array available for use with the probe style illustrated in FIGS. 7A-7B.

In some embodiments, the radius of curvature of the array in the probe of FIG. 7 may be adequately shallow to allow for imaging a variety of body tissues (e.g., abdomen, pelvis, peripheries, etc.). The probe of FIG. 7 can image in 2D as a curvilinear probe using a concave 1D array such as that shown in FIG. 7C. The probe of FIG. 7 may also be operated in 3D or 4D imaging modalities using a 3D piezoelectric array such as that shown in FIG. 7D or a CMUT array such as that shown in FIG. 7E.

Figure 7F:
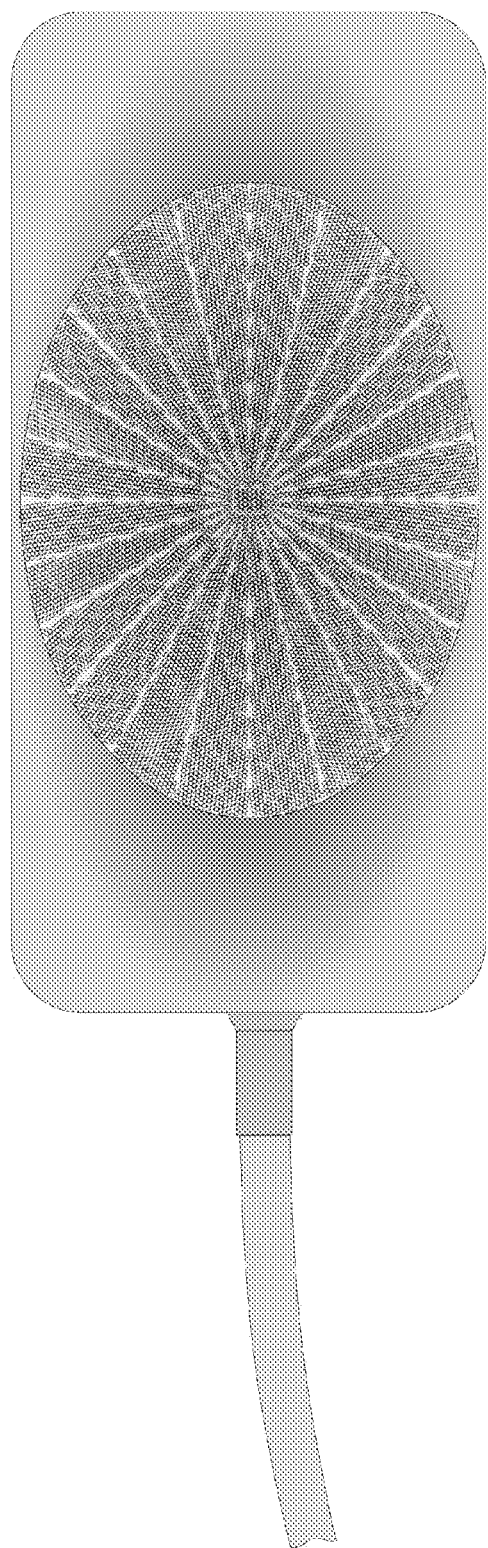
FIG. 7F is a bottom view of a concave curved transducer array (e.g., 3D or CMUT) arranged in an elliptical pattern, as used in a probe such as that shown in FIGS. 7A-7B.

FIG. 7F illustrates an embodiment of a 3D piezoelectric or CMUT array that may be used to collect cylindrical volumes of data. The array of FIG. 7F may be operated according to the methods discussed above with reference to FIGS. 4A-4E.

In some embodiments, the probe of FIG. 7F may be configured and/or controlled to function as an annular array in which transducer elements are fired in concentric patterns to improve imaging depth.

Figure 7G:
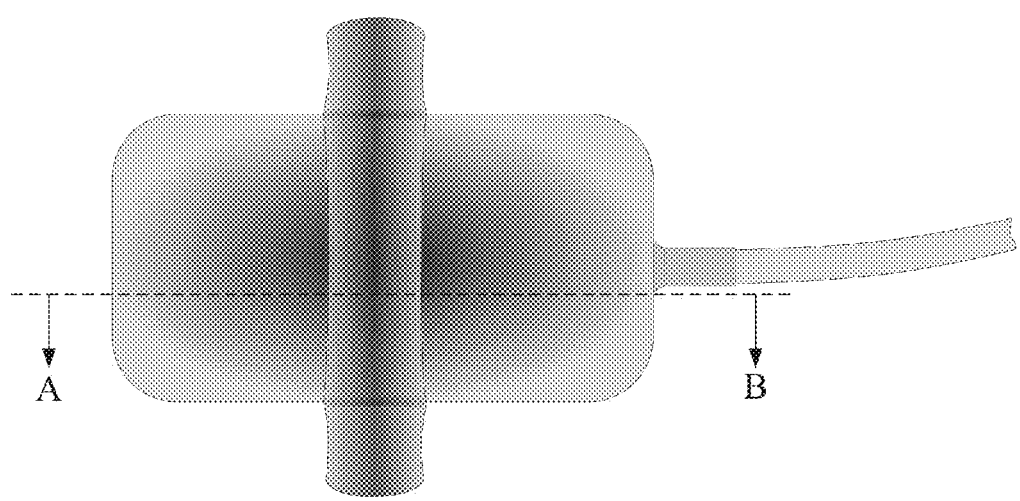
FIG. 7G is a plan view of a concave array probe housing identifying the section line for FIG. 7H.
Figure 7H:
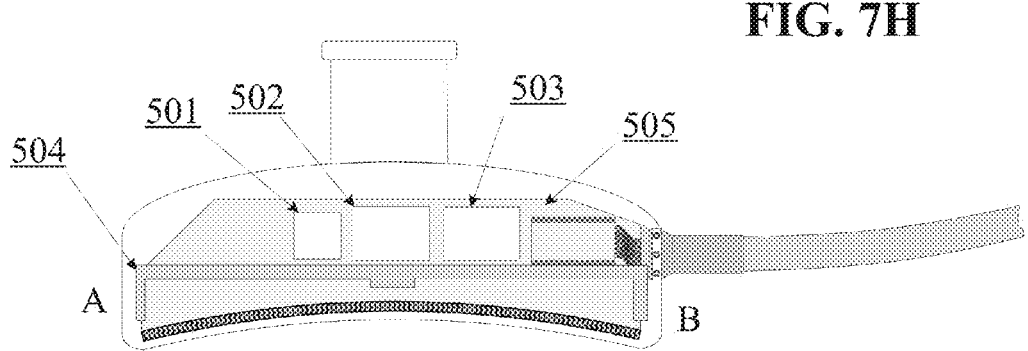
FIG. 7H is a sectional view of the concave array probe housing of FIG. 7G taken along line A-B. This embodiment illustrates flex connectors and cabling connections on the right side or bottom of the probe. A calibration chip, synchronization module, probe position displacement sensor are also shown in the probe handle.

As shown in FIG. 7G, embodiments of probes such as that shown in FIGS. 7-7G may be constructed substantially similarly to probes discussed above with reference to FIGS. 5 and 6. For example, the FIG. 7 probe may include a backing plate 508, a flex connector 505, transmit synchronizer module 502, a probe position displacement sensor 503, a Calibration Chip 501, and any other suitable components.

Figure 8:
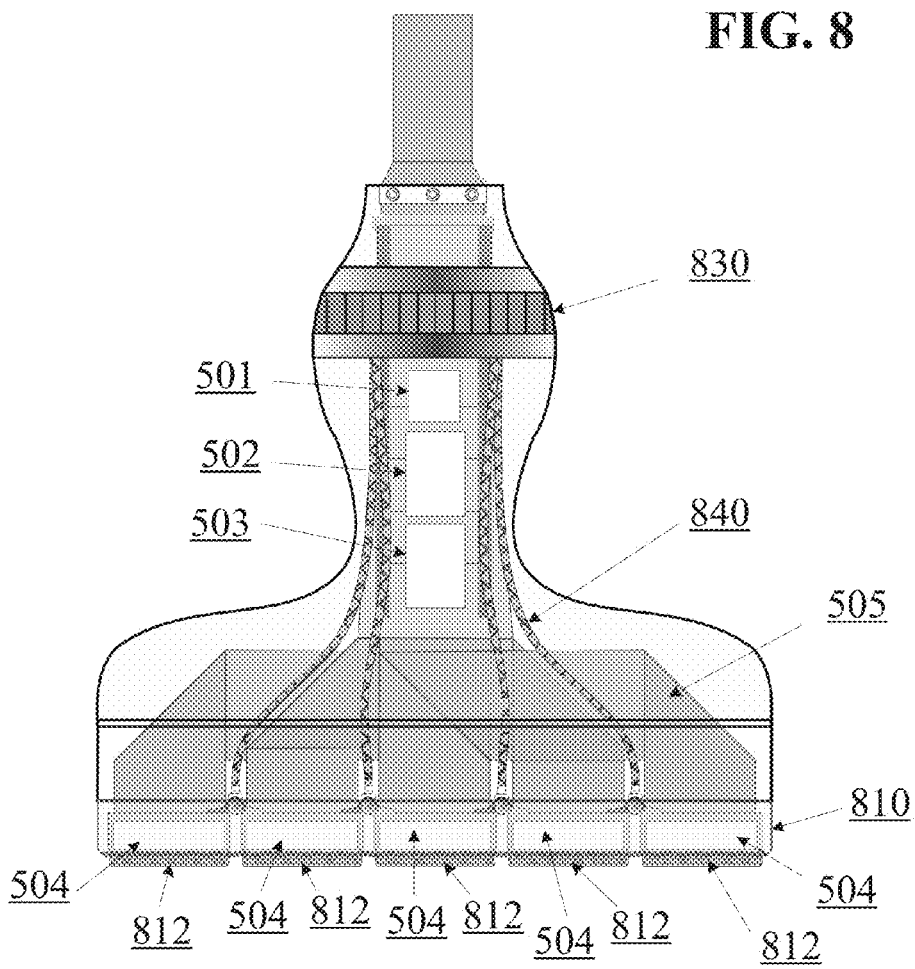
FIG. 8 is a diagram showing an embodiment of an adjustable ultrasound probe. This version of an adjustable probe has five arrays, each having an associated flex connector. A calibration chip, synchronization module, probe position displacement sensor are also shown in the probe handle.

FIG. 8 illustrates one embodiment of an adjustable probe with a plurality of adjustable ultrasound arrays that may be adjusted to conform to a variety of surface shapes. For example, a sonographer may place the adjustable probe around a physiology of interest, allowing the arrays to conform to the shape of the structure. The sonographer may then lock the arrays into the conformed orientations. Once the arrays are locked in a desired orientation, the probe may be calibrated using a suitable calibration system and the probe may be used to image the physiology of interest.

Figure 8A:
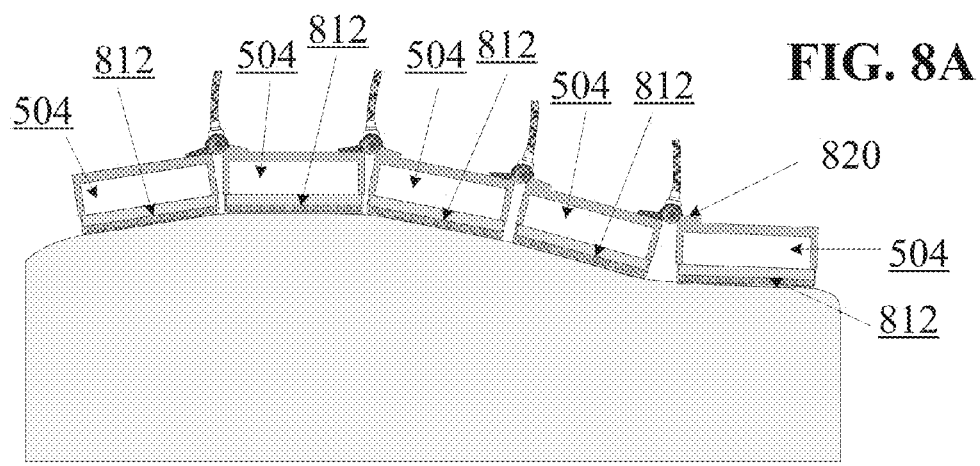
FIG. 8A is a diagram showing the five arrays of the probe of FIG. 8 deployed in a custom contoured arrangement to match the desired physiology.

FIG. 8 illustrates one embodiment of an array adjustment and locking mechanism. Many other mechanical adjustment and locking mechanisms may alternatively be used. The mechanism of FIG. 8 includes a bellows 810 configured to provide positive pressure on the five adjustable arrays 812, biasing the arrays toward the orientation shown in FIG. 8. The backing blocks 504 of each of the adjustable arrays may be connected to each other by hinge mechanisms 820. As the sonographer places pressure on the probe to overcome the resistance of the bellows, the arrays conform to the shape of the desired physiology as illustrated in FIG. 8A.

Figure 8B:
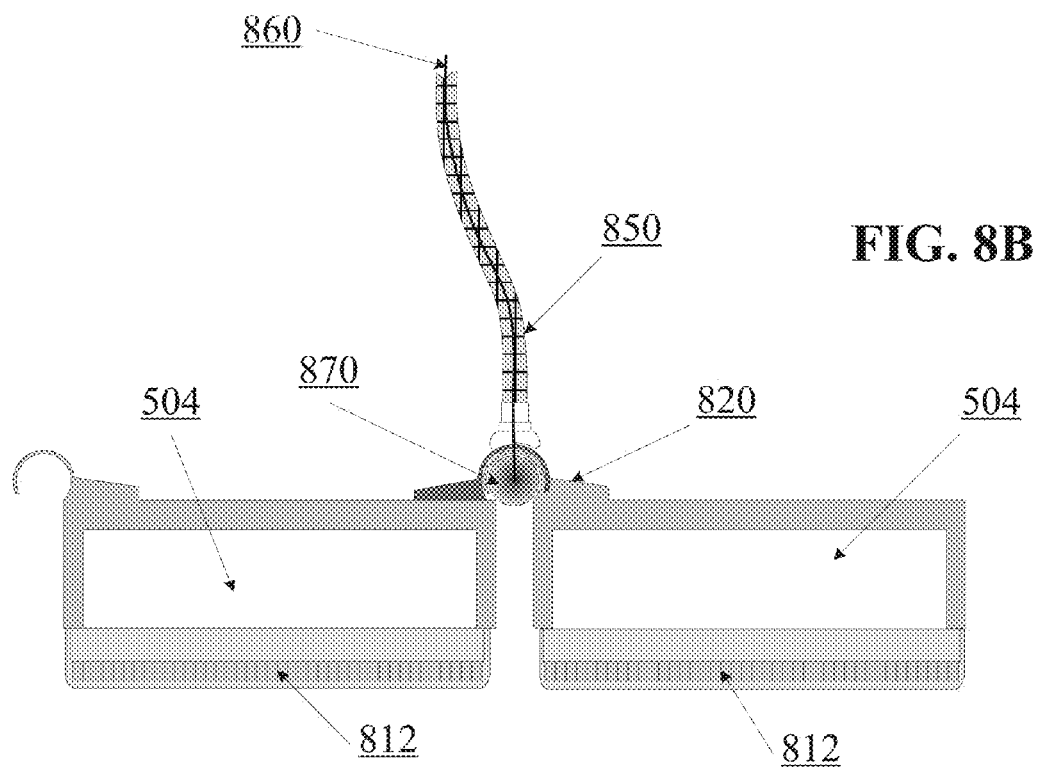
FIG. 8B is a side view of two of the arrays of the probe of FIG. 8, showing details of an embodiment of adjustable hinges between the arrays and a tension cable. The adjustable hinges are shown connected to the backing block of each array.

At this time, the sonographer may turn the tightening handle 830 to lock all of the hinge mechanisms in place. The tightening handle may be connected to the hinge mechanisms 820 via hinge cables 840. The cables 840 may comprise an outer conduit 850 and an inner tension wire 860 as illustrated in FIG. 8B. The wire 860 may be attached to a pivot pin 870, and configured such that when the locking ring 830 is rotated, the wire 860 drawn upwards, compressing the pivot pin 870 and hinge 820 for the entire length of the hinge. When the conformed position no longer needed, the tightening handle may be relaxed and the bellows may push all of the arrays out to their fully extended position.

Figure 8C:
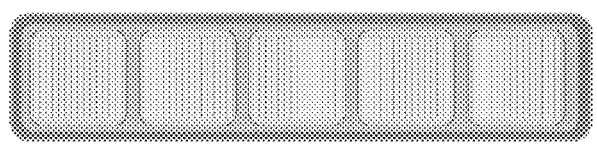
FIG. 8C is a bottom view illustrating an embodiment of the individual arrays (e.g., 1D or 1.5D) in a probe such as that shown in FIG. 8.
Figure 8D:
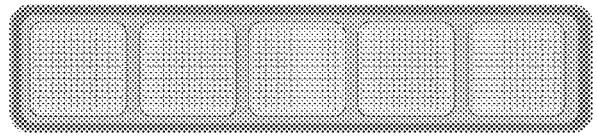
FIG. 8D is a bottom view illustrating an embodiment of the individual arrays as matrix arrays (e.g., 2D) in a probe such as that shown in FIG. 8.
Figure 8E:
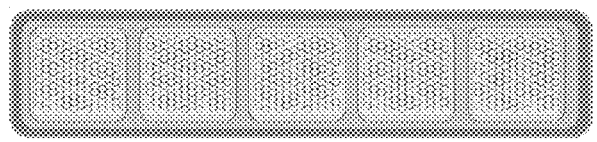
FIG. 8E is a bottom view illustrating an embodiment of the individual arrays as CMUT arrays in a probe such as that shown in FIG. 8.

In some embodiments, each array 812 in the adjustable probe may have its own backing block 504 and flex connector 505. The type of arrays used in an adjustable array can vary. For example, FIG. 8C illustrates an adjustable probe with 1D probes. In some embodiments, an adjustable probe may include transducer arrays of different frequencies. For instance, in some embodiments arrays that use lower frequencies may be located on lateral ends of the probe, and arrays using higher frequencies may be located towards the center. 2D or CMUT arrays may also be used, as shown in FIGS. 8D and 8E. In some embodiments, each array 812 of an adjustable probe may have a planar shape. In other embodiments, each array 812 may have a concave shape with curvature in one or two or more axes.

An adjustable probe may include similar electronic components to other static-position probes described herein. For example, an adjustable probe may include a Calibration Chip 501, a transmit synchronizer module 502 and probe position displacement sensor 503.

An adjustable probe such as that shown in FIG. 8 may be operated in 2D, 3D or 4D imaging modalities according to any of the methods described herein.

Terms such as "optimized," "optimum," "precise," "exact" and similar terms used in relation to quantitative parameters are merely intended to indicate design parameters which may be controlled or varied in accordance with general engineering principles. Use of these terms is not intended to imply or require that the parameters or components thereof are designed for the best possible or theoretical performance.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

What is claimed is:

1. A method of producing a volumetric data set representing a region of interest within an object to be imaged, the method comprising:
placing an ultrasound probe having an array of transducer elements in contact with the object to be imaged;
transmitting an un-focused ultrasound pulse into the object with the ultrasound probe from a first transmit aperture comprising a first single transducer element;
adjusting a size or shape of a first receive aperture by assigning a first plurality of transducer elements to the first receive aperture;
adjusting a size or shape of a second receive aperture by assigning a second plurality of transducer elements to the second receive aperture;
receiving volumetric data from the un-focused ultrasound pulse at each of the first plurality of transducer elements of the first receive aperture;
receiving volumetric data from the un-focused ultrasound pulse at each of the second plurality of transducer elements of the second receive aperture;
storing the volumetric data received by each of the first and second plurality of transducer elements of the first and second receive apertures;
coherently averaging the volumetric data from each of the first plurality of transducer elements of the first receive aperture to create a first volume;
coherently averaging the volumetric data from each of the second plurality of transducer elements of the second receive aperture to create a second volume; and
incoherently averaging the first and second volumes to create a 3D volume.

2. The method of claim 1, wherein the first plurality of transducer elements of the first receive aperture comprises at least some transducer elements spaced from other transducer elements in three dimensions.

3. The method of claim 1, wherein the array of transducer elements has a concave shape.

4. The method of claim 1, wherein the array of transducer elements is a continuous array with a concave curvature in two dimensions.

5. The method of claim 1, wherein the size of the first receive aperture is different than the size of the second receive aperture.

6. The method of claim 5, wherein the shape of the first receive aperture is different than the shape of the second receive aperture.

7. The method of claim 1, wherein the size of each of the first receive aperture and the second receive aperture is selected such that speed of sound variations in paths from scatterers to each of the receive elements avoid phase cancellation when coherent averaging is used.

8. The method of claim 1, further comprising changing a size of the first receive aperture in response to a user input.

9. The method of claim 6, wherein the first receive aperture has a square shape.

10. The method of claim 1, further comprising transmitting a second un-focused ultrasound pulse into the object with the ultrasound probe from a second transmit aperture comprising a second single transducer element located separately from the first single transducer element of the first transmit aperture and from the first and second receive apertures.

* * * * *